United States Patent
Voyer et al.

(10) Patent No.: US 10,415,028 B2
(45) Date of Patent: Sep. 17, 2019

(54) VARIANTS OF THERMOVIBRIO AMMONIFICANS CARBONIC ANHYDRASE AND CO$_2$ CAPTURE METHODS USING THERMOVIBRIO AMMONIFICANS CARBONIC ANHYDRASE VARIANTS

(71) Applicant: CO2 SOLUTIONS INC., Québec (CA)

(72) Inventors: Normand Voyer, Neuville (CA); Richard Daigle, Lévis (CA); Éric Madore, Québec (CA); Sylvie Fradette, Lévis (CA)

(73) Assignee: CO2 Solutions Inc., Quebec (CA)

(*) Notice: Subject to any disclaimer, the term of this patent is extended or adjusted under 35 U.S.C. 154(b) by 0 days.

(21) Appl. No.: 15/757,301

(22) PCT Filed: Sep. 2, 2016

(86) PCT No.: PCT/CA2016/051049
§ 371 (c)(1),
(2) Date: Mar. 2, 2018

(87) PCT Pub. No.: WO2017/035667
PCT Pub. Date: Mar. 9, 2017

(65) Prior Publication Data
US 2019/0136220 A1  May 9, 2019

Related U.S. Application Data

(60) Provisional application No. 62/323,150, filed on Apr. 15, 2016, provisional application No. 62/213,941, filed on Sep. 3, 2015.

(51) Int. Cl.
| | | |
|---|---|---|
| *C12N 9/88* | (2006.01) | |
| *B01D 53/62* | (2006.01) | |
| *B01D 53/14* | (2006.01) | |
| *C12N 15/74* | (2006.01) | |
| *B01D 53/84* | (2006.01) | |

(52) U.S. Cl.
CPC ............ *C12N 9/88* (2013.01); *B01D 53/1475* (2013.01); *B01D 53/1493* (2013.01); *B01D 53/62* (2013.01); *B01D 53/84* (2013.01); *C12N 15/74* (2013.01); *B01D 2252/204* (2013.01); *B01D 2252/205* (2013.01); *B01D 2257/504* (2013.01); *C12Y 402/01001* (2013.01)

(58) Field of Classification Search
CPC ....................................................... C12N 9/88
USPC ....................................................... 435/232
See application file for complete search history.

(56) References Cited

U.S. PATENT DOCUMENTS

2013/0052720 A1  2/2013  Fradette et al.
2013/0149771 A1  6/2013  Borchert

FOREIGN PATENT DOCUMENTS

WO  WO 2015/056858 A1  4/2015

OTHER PUBLICATIONS

International Search Report received in PCT Application No. PCT/CA2016/051049, dated Oct. 7, 2016.
Written Opinion received in PCT Application No. PCT/CA2016/051049, dated Oct. 7, 2016.

*Primary Examiner* — Tekchand Saidha
(74) *Attorney, Agent, or Firm* — Knobbe, Martens, Olson & Bear, LLP

(57) ABSTRACT

The present description relates to recombinant or engineered carbonic anhydrase polypeptides, variants, and functional derivatives thereof, having improved properties that make them advantageous for use in CO$_2$ capture operations (e.g., CO$_2$ capture solvents, alkaline pH, and/or elevated temperatures), as well as polynucleotides and vectors encoding same. The present description also relates to methods, processes and systems for CO$_2$ capture which make use of the recombinant or engineered carbonic anhydrase polypeptides, variants, and functional derivatives thereof.

20 Claims, 14 Drawing Sheets

Specification includes a Sequence Listing.

Figure 1

```
  1 GTGAAGAGAGTATTG GTTACCCTCGGGGCT GTTGCAGCACTTGCA ACGGGCGCGGTTGCA
  1 M K R V L   V T L G A   V A A L A   T G A V A

61 GGTGGAGGAGCCCAC TGGGGTTATTCCGGC AGCATCGGGCCGGAG CACTGGGGAGATTTA
 21 G G G A H   W G Y S G   S I G P E   H W G D L

121 AGCCCCGAATACCTT ATGTGTAAAATCGGT AAGAACCAATCGCCC ATAGATATTAACAGC
 41 S P E Y L   M C K I G   K N Q S P   I D I N S

181 GCCGATGCGGTTAAG GCGTGTCTTGCTCCC GTTAGCGTCTACTAC GTTTCAGACGCAAAG
 61 A D A V K   A C L A P   V S V Y Y   V S D A K

241 TACGTTGTTAACAAC GGCCACACAATTAAG GTTGTTATGGGGGGA AGGGGTTACGTGGTT
 81 Y V V N N   G H T I K   V V M G G   R G Y V V

301 GTTGACGGTAAGCGC TTTTACCTGAAGCAG TTCCACTTTCACGCC CCCAGCGAGCACACC
101 V D G K R   F Y L K Q   F H F H A   P S E H T

361 GTTAACGGCAAGCAC TACCCCTTTGAAGCC CACTTCGTCCACCTT GATAAAAACGGGAAC
121 V N G K H   Y P F E A   H F V H L   D K N G N

421 ATAACGGTCCTTGGC GTTTTCTTTAAGGTT GGGAAGGAAAACCCC GAGCTTGAGAAGGTG
141 I T V L G   V F F K V   G K E N P   E L E K V

481 TGGCGTGTTATGCCC GAGGAGCCGGGTCAG AAGAGACACCTTACC GCAAGAATCGACCCG
161 W R V M P   E E P G Q   K R H L T   A R I D P

541 GAGAAGCTCTTGCCC GAGAACAGGGACTAC TACAGATACTCCGGC TCTCTCACCACACCG
181 E K L L P   E N R D Y   Y R Y S G   S L T T P

601 CCCTGCTCGGAAGGG GTTAGGTGGATTGTG TTTAAAGAGCCGGTT GAGATGTCTCGGGAG
201 P C S E G   V R W I V   F K E P V   E M S R E

661 CAGCTTGAGAAGTTC AGGAAAGTTATGGGC TTTGACAACAACAGG CCGGTTCAGCCCCTT
221 Q L E K F   R K V M G   F D N N R   P V Q P L

721 AATGCAAGGAAGGTT ATGAAGTAG    (SEQ ID NO: 1)
241 N A R K V   M K *         (SEQ ID NO: 2)
```

Figure 15

Table 4 – Variants identified by directed evolution screening process by TACA residue position

| Position | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| SEQ ID NO: 7 | M | E | H | E | W | G | Y | S | G | S | I | G | P | E | H | W | G | D | L | S |
| Mutation |  | Q |  |  | C |  | C | C | C |  |  | D | Q |  |  | C | C | V | S |  |
| Mutation |  | V |  |  | R |  | F | R | P |  |  | R |  |  |  | G |  |  |  |  |
| Mutation |  |  |  |  |  |  | H |  | N* |  |  | V |  |  |  | R |  |  |  |  |

| Position | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| SEQ ID NO: 7 | P | E | Y | L | M | C | K | I | G | K | N | Q | S | P | I | D | I | N | S | A |
| Mutation | L | K |  |  |  |  | T* |  |  |  | C |  |  |  |  |  |  |  |  |  |
| Mutation | K | L |  |  |  |  |  |  |  |  |  |  |  |  |  |  |  |  |  |  |
| Mutation | D* | P |  |  |  |  |  |  |  |  |  |  |  |  |  |  |  |  |  |  |
| Mutation | N* | N* |  |  |  |  |  |  |  |  |  |  |  |  |  |  |  |  |  |  |
| Mutation | Q* |  |  |  |  |  |  |  |  |  |  |  |  |  |  |  |  |  |  |  |  |
| Mutation | V* |  |  |  |  |  |  |  |  |  |  |  |  |  |  |  |  |  |  |  |  |
| Mutation | G* |  |  |  |  |  |  |  |  |  |  |  |  |  |  |  |  |  |  |  |  |

| Position | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|
| SEQ ID NO: 7 | D | A | V | K | A | C | L | A | P | V | S | V | Y | Y | V | S | D | A | K | Y |
| Mutation |  |  |  |  |  |  |  |  |  | M* | I | I |  |  |  |  |  |  |  |  |

| Position | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|
| SEQ ID NO: 7 | V | V | N | N | G | H | T | I | K | V | V | M | G | G | R | G | Y | V | V | V |
| Mutation |  |  |  |  |  |  |  |  |  |  |  |  | C |  |  | D | D |  |  |  |

| Position | 81 | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|---|
| SEQ ID NO: 7 | D | G | K | R | F | Y | L | K | Q | F | H | F | H | A | P | S | E | H | T | V |
| Mutation |  | S |  |  |  |  |  |  |  |  |  |  |  |  |  |  |  |  |  |  |

| Position | 101 | 102 | 103 | 104 | 105 | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|---|---|---|---|---|
| SEQ ID NO: 7 | N | G | K | H | Y | P | F | E | A | H | F | V | H | L | D | K | N | G | N | I |
| Mutation | Q |  | M |  |  |  |  |  |  |  |  |  |  |  |  | N | N | Q |  |  |

| Position | 121 | 122 | 123 | 124 | 125 | 126 | 127 | 128 | 129 | 130 | 131 | 132 | 133 | 134 | 135 | 136 | 137 | 138 | 139 | 140 |
|---|---|---|---|---|---|---|---|---|---|---|---|---|---|---|---|---|---|---|---|---|
| SEQ ID NO: 7 | T | V | L | G | V | F | F | K | V | G | K | E | N | P | E | L | E | K | V | W |
| Mutation |  |  |  |  | A | L |  |  |  |  | I |  |  |  |  |  |  | N |  |  |
| Mutation |  |  |  |  |  |  |  |  |  |  |  |  |  |  |  |  |  | R* |  |  |

| Position | 141 | 142 | 143 | 144 | 145 | 146 | 147 | 148 | 149 | 150 | 151 | 152 | 153 | 154 | 155 | 156 | 157 | 158 | 159 | 160 |
|---|---|---|---|---|---|---|---|---|---|---|---|---|---|---|---|---|---|---|---|---|
| SEQ ID NO: 7 | R | V | M | P | E | E | P | G | Q | K | R | H | L | T | A | R | I | D | P | E |
| Mutation | H | I* |  |  |  |  |  |  |  | M* | C |  |  |  |  | E |  | G* |  |  |

| Position | 161 | 162 | 163 | 164 | 165 | 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|---|---|---|---|---|---|
| SEQ ID NO: 7 | K | L | L | P | E | N | R | D | Y | Y | R | Y | S | G | S | L | T | T | P | P |
| Mutation |  |  |  |  |  |  | S |  |  |  |  |  | C |  |  |  |  |  |  |  |

| Position | 181 | 182 | 183 | 184 | 185 | 186 | 187 | 188 | 189 | 190 | 191 | 192 | 193 | 194 | 195 | 196 | 197 | 198 | 199 | 200 |
|---|---|---|---|---|---|---|---|---|---|---|---|---|---|---|---|---|---|---|---|---|
| SEQ ID NO: 7 | C | S | E | G | V | R | W | I | V | F | K | E | P | V | E | M | S | R | E | Q |
| Mutation | Y |  |  |  |  |  |  |  |  | C |  |  |  |  | S* |  |  |  |  |  |
| Mutation |  |  |  |  |  |  |  |  |  | M* |  |  |  |  |  |  |  |  |  |  |

| Position | 201 | 202 | 203 | 204 | 205 | 206 | 207 | 208 | 209 | 210 | 211 | 212 | 213 | 214 | 215 | 216 | 217 | 218 | 219 | 220 |
|---|---|---|---|---|---|---|---|---|---|---|---|---|---|---|---|---|---|---|---|---|
| SEQ ID NO: 7 | L | E | K | F | R | K | V | M | G | F | D | N | N | R | P | V | Q | P | L | N |
| Mutation |  |  |  |  |  | T* |  |  |  |  |  |  |  |  |  |  |  |  |  |  |

| Position | 221 | 222 | 223 | 224 | 225 | 226 |
|---|---|---|---|---|---|---|
| SEQ ID NO: 7 | A | R | K | V | M | K |

■ Shows a half-life at least 150% that of SEQ ID NO: 7 in at least one of the 3 test conditions of Table 3.
□ Shows a half-life at least 125% that of SEQ ID NO: 7 in at least one of the 3 test conditions of Table 3.
  Shows a half-life less than 125% that of SEQ ID NO: 7 in at least one of the 3 test conditions of Table 3.
* Not characterized as a single mutant

VARIANTS OF THERMOVIBRIO AMMONIFICANS CARBONIC ANHYDRASE AND CO₂ CAPTURE METHODS USING THERMOVIBRIO AMMONIFICANS CARBONIC ANHYDRASE VARIANTS

CROSS-REFERENCE TO RELATED APPLICATIONS

This application is a U.S. National Phase Application of PCT International Application No. PCT/CA2016/051049, filed on Sep. 2, 2016, designating the United States of America, which claims priority to U.S. Provisional Application Ser. No. 62/213,941, filed on Sep. 3, 2015, and U.S. Provisional Application Ser. No. 62/323,150, filed on Apr. 15, 2016.

INCORPORATION OF THE SEQUENCE LISTING

The present application contains a Sequence Listing, which is being submitted via EFS-Web on even date herewith. The Sequence Listing is submitted in a file entitled "SeqListing_ROBCA52-005APC.txt," which was created on Feb. 27, 2018, and is approximately 20 kb in size. This Sequence Listing is hereby incorporated by reference.

TECHNICAL FIELD

The technical field relates to $CO_2$ capture, *Thermovibrio ammonificans* carbonic anhydrase (TACA) and/or variants and use thereof for catalyzing the hydration reaction of $CO_2$ into bicarbonate and hydrogen ions and/or catalyzing the desorption reaction to produce a $CO_2$ gas.

BACKGROUND

Increasingly dire warnings of the dangers of climate change by the world's scientific community combined with greater public awareness and concern over the issue has prompted increased momentum towards global regulation aimed at reducing man-made greenhouse gas (GHGs) emissions, most notably carbon dioxide. Ultimately, a significant cut in North American and global $CO_2$ emissions will require reductions from the electricity production sector, the single largest source of $CO_2$ worldwide. According to the International Energy Agency's (IEA) GHG Program, as of 2006 there were nearly 5,000 fossil fuel power plants worldwide generating nearly 11 billion tons of $CO_2$, representing nearly 40% of total global anthropogenic $CO_2$ emissions. Of these emissions from the power generation sector, 61% were from coal fired plants. Although the long-term agenda advocated by governments is replacement of fossil fuel generation by renewables, growing energy demand, combined to the enormous dependence on fossil generation in the near term dictates that this fossil base remain operational. Thus, to implement an effective GHG reduction system will require that the $CO_2$ emissions generated by this sector be mitigated, with carbon capture and storage (CCS) providing one of the best known solutions.

The CCS process removes $CO_2$ from a $CO_2$ containing gas and involves the production of a highly concentrated $CO_2$ gas stream which is compressed and transported to a geologic sequestration site. This site may be a depleted oil field, a saline aquifer or any suitable storage site. Sequestration in oceans and mineral carbonation are two alternate ways to sequester $CO_2$ that are in the research phase. Captured $CO_2$ can also be used for enhanced oil recovery or for carbonation of alkaline waste streams for sequestration as mineral solids.

Conventional technologies for $CO_2$ capture are based on the use of aqueous amines (e.g. alkanolamines) and carbonates solutions which are circulated through two main distinct units: an absorption unit coupled to a desorption (or stripping) unit. However, in the context of low $CO_2$ partial pressures encountered in gases from combustion, these conventional technologies give rise to processes with high energy penalty and thus high operational expenditure, as it is the case with monoethanolamine (MEA), or processes with high capital expenditure, as for the case of kinetically limited absorption solutions resulting in large equipment such as with methydiethanolamine (MDEA) for example. Higher pressure $CO_2$ separation from process streams seen in $H_2$ production or gasification is typically usually easier to achieve due to the higher pressures in such processes.

Carbonic anhydrase is an enzyme that has been used for $CO_2$ absorption applications. Carbonic anhydrase is not just a single enzyme form, but a broad group of metalloproteins that exists in genetically unrelated families of isoforms, α, β, γ, δ and ε. Different classes, isoforms and variants of carbonic anhydrase have been used in order to catalyze the hydration reaction of $CO_2$ into bicarbonate and hydrogen ions and the bicarbonate dehydration reaction into $CO_2$ and water, as follows:

$$CO_2 + H_2O \leftrightarrow H^+ + HCO_3^- \quad \text{(Reaction 1)}$$

Under optimum conditions, the catalyzed turnover rate of the hydration reaction can reach $1 \times 10^6$ molecules/second.

However, there are several challenges related to the use of carbonic anhydrase in $CO_2$ capture operations. For instance, the temperature stability in time, the chemical resistance and the activity of the carbonic anhydrase under process conditions are factors that have an impact on process design, process performance and operating costs.

There is thus a need to overcome at least some of the challenges related to the use of carbonic anhydrase for $CO_2$ capture.

SUMMARY

The present description generally relates to recombinant or engineered carbonic anhydrase (CA) polypeptides, variants, and functional derivatives thereof, having improved properties that make them advantageous for use in $CO_2$ capture operations. Starting from the wild-type sequence of a carbonic anhydrase from *Thermovibrio ammonificans* (TACA), directed evolution techniques were employed to identify variants having improved performance in conditions suitable for $CO_2$-capture (e.g., $CO_2$ capture solvents, alkaline pH, and/or elevated temperatures). This approached identified a number of amino acid positions, particularly in the N-terminal region of the protein (e.g., residues 1 to 25), which may be engineered to obtain variants having improved properties for $CO_2$ capture.

Accordingly, the present description relates to the following implementations:

1. A recombinant carbonic anhydrase polypeptide comprising:
   (a) an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identity with SEQ ID NO: 2, 4, 6, 7, or 10, or a functional derivative thereof;

(b) an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identity with SEQ ID NO: 2, 4, 6, 7, or 10, and comprising at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, or forty-four amino acid difference(s) relative to SEQ ID NO: 7 at a position corresponding to X2, X5, X7, X8, X9, X12, X13, X16, X17, X18, X19, X21, X22, X27, X31, X50, X51, X52, X73, X76, X77, X82, X101, X103, X115, X116, X117, X125, X131, X126, X138, X141, X142, X150, X151, X156, X158, X167, X173, X181, X190, X193, X206, X227, or any combination thereof;

(c) an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identity with SEQ ID NO: 2, 4, 6, 7, or 10, and comprising at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, or forty-four amino acid difference(s) relative to SEQ ID NO: 7 at a position corresponding to E2X, W5X, Y7X, S8X, G9X, G12X, P13X, W16X, G17X, D18X, L19X, P21X, E22X, K27X, N31X, V50X, S51X, V52X, G73X, G76X, Y77X, G82X, N101X, K103X, D115X, K116X, N117X, V125X, F126X, K131X, K138X, R141X, V142X, K150X, R151X, R156X, D158X, R167X, S173X, X181X, F190X, P193X, K206X, Ter227X, or any combination thereof, wherein C, D, E, F, G, K, L, N, P, Q, R, S, V, W, Y are known amino acids, Ter is a translation termination codon and X is any amino acid, or a functional derivative thereof;

(d) an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identity with SEQ ID NO: 2, 4, 6, 7, or 10, and comprising at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, or forty-four amino acid difference(s) relative to SEQ ID NO: 7, wherein said difference comprises X2Q, X2V, X5C, X5R, X7C, X7F, X7H, X8C, X8R X9C, X9P, X9N, X12D, X12R, X12V, X13Q, X16C, X16G, X16R, X17C, X18V, X19S, X21L, X21K, X21D, X21N, X21Q, X21V, X21G, X22K, X22L, X22P, X22N, X27T, X31C, X50M, X51I, X52I, X73C, X76D, X77D, X82S, X101Q, X103M, X115N, X116N, X117Q, X125A, X126L, X131I, X138N, X138R, X141H, X142I, X150M, X151C, X156E, X158G, X167S, X173C, X181Y, X190C, X190M, X193S, X206T, Ter227YG, or any combination thereof, wherein Ter is a translation termination codon and A, C, D, E, G, H, I, K, L, M, N, P, Q, R, S, T, V, Y are known amino acids and X is any amino acid, or a functional derivative thereof, (e) an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identity with SEQ ID NO: 2, 4, 6, 7, or 10, and comprising at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, or forty-four amino acid difference(s) relative to SEQ ID NO: 7, wherein said difference comprises E2Q, E2V, W5C, W5R, Y7C, Y7F, Y7H, S8C, S8R, G9C, G9P, G9N, G12D, G12R, G12V, G13Q, W16C, W16G, W16R, G17C, D18V, L19S, P21L, P21K, P21D, P21N, P21Q, P21V, P21G, E22K, E22L, E22P, E22N, K27T, N31C, V50M, S51I, V52I, G73C, G76D, Y77D, G82S, N101Q, K103M, D115N, K116N, N117Q, V125A, F126L, K131I, K138N, K138R, R141H, V142I, K150M, R151C, R156E, D158G, R167S, S173C, C181Y, F190C, F190M, P193S, K206T, Ter227YG, or any combination thereof, wherein A, C, D, E, F, G H, I, K, L, M, N, P, Q, R, S, T, V, W and Y are known amino acids, Ter is the translation termination codon, and X is any other amino acid, or a functional derivative thereof;

(f) the amino acid sequence of any one of (a) to (e) comprising one or more conservative mutations relative to SEQ ID NO: 7; or (g) an amino acid sequence which is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO: 7, and comprises at least of the amino acid substitutions: E2Q, E2V, W5C, W5R, Y7C, Y7F, Y7H, S8C, S8R, G9C, G9P, G9N, G12D, G12R, G12V, G13Q, W16C, W16G, W16R, G17C, D18V, L19S, P21L, P21K, P21D, P21N, P21Q, P21V, P21G, E22K, E22L, E22P, E22N, K27T, N31C, V50M, S51I, V52I, G73C, G76D, Y77D, G82S, N101Q, K103M, D115N, K116N, N117Q, V125A, F126L, K131I, K138N, K138R, R141H, V142I, K150M, R151C, R156E, D158G, R167S, S173C, C181Y, F190C, F190M, P193S, K206T, or Ter227YG, wherein said recombinant polypeptide has carbonic anhydrase activity.

2. The recombinant polypeptide of implementation 1, wherein the amino acid sequence of any one of (a) to (f) is different from SEQ ID NO: 2, 4, 6, 7, or 10.

3. A recombinant carbonic anhydrase polypeptide comprising an amino acid sequence at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO: 7, and a least one amino acid difference relative to SEQ ID NO: 7 at a position corresponding to residues 1 to 25.

4. The recombinant polypeptide of implementation 3, wherein said amino acid difference is at a position corresponding to position 2, 5, 7, 8, 9, 12, 13, 16, 17, 18, 19, 21, 22, or any combination thereof, of SEQ ID NO: 7.

5. The recombinant polypeptide of any one of implementations 1 to 4, which has an improved property relative to the same property of the polypeptide of SEQ ID NO: 2, 4, 6, 7, or 10, wherein said improved property is:
  (a) Improved stability, activity, and/or solubility in presence of sodium ion;
  (b) Improved stability, activity, and/or solubility in presence of potassium ion;
  (c) Improved stability, activity, and/or solubility in presence of carbonate ion;
  (d) Improved stability, activity, and/or solubility under high pH conditions;
  (e) Improved stability, activity, and or solubility under high temperature conditions;
  (f) Improved stability, activity, and/or solubility under high ionic strength;
  (g) Improved pH-activity profile;
  (h) Improved pH-activity profile under high ionic strength;
  (i) Improved stability in an amine-based $CO_2$ capture solvent;
  (j) Improved stability in an amino-acid-based $CO_2$ capture solvent; or
  (k) Improved stability in a potassium or sodium salt of an amino-acid based $CO_2$ capture solvent.

6. A recombinant carbonic anhydrase polypeptide comprising an amino acid sequence at least 85%, 86%, 87%, 88%, 89%, 90%, 91%, 92%, 93%, 94%, 95%, 96%, 97%, 98%, 99%, or 99.5% identical to SEQ ID NO: 2, 4, 6, 7 or 10, and having:
  (a) a cysteine or arginine at a position corresponding to position 8 of SEQ ID NO: 7;
  (b) a cysteine, proline, or asparagine at a position corresponding to position 9 of SEQ ID NO: 7;
  (c) a lysine, leucine, proline, or asparagine at a position corresponding to position 22 of SEQ ID NO: 7; or
  (d) any combination of (a) to (c),
wherein said recombinant polypeptide has carbonic anhydrase activity and exhibits improved stability in a $CO_2$ capture solvent as compared to the polypeptide of SEQ ID NO: 2, 4, 6, 7, or 10.

7. The recombinant polypeptide of implementation 6, wherein said polypeptide further comprises one or more of the amino acid substitutions corresponding to E2Q, E2V, W5C, W5R, Y7C, Y7F, Y7H, S8C, S8R, G9C, G9P, G9N, G12D, G12R, G12V, G13Q, W16C, W16G, W16R, G17C, D18V, L19S, P21L, P21K, P21D, P21N, P21Q, P21V, P21G, E22K, E22L, E22P, E22N, K27T, N31C, V50M, S51I, V52I, G73C, G76D, Y77D, G82S, N101Q, K103M, D115N, K116N, N117Q, V125A, F126L, K131I, K138N, K138R, R141H, V142I, K150M, R151C, R156E, D158G, R167S, S173C, C181Y, F190C, F190M, P193S, K206T, or Ter227YG, of SEQ ID NO: 7.

8. A polynucleotide comprising a nucleotide sequence encoding the carbonic anhydrase polypeptide as defined in any one of implementations 1 to 7.

9. The polynucleotide of implementation 8, operably linked to a heterologous promoter.

10. An expression or cloning vector comprising the polynucleotide as defined in implementation 8 or 9.

11. A transgenic cell comprising the polynucleotide as defined in implementation 9, or the expression or cloning vector as defined in implementation 10.

12. The recombinant carbonic anhydrase polypeptide as defined in any one of implementations 1 to 7, for use in removing $CO_2$ from a $CO_2$-containing effluent or gas.

13. Use of the carbonic anhydrase polypeptide as defined in any one of implementations 1 to 7 for removing $CO_2$ from a $CO_2$-containing effluent or gas.

14. A process for treating a $CO_2$-containing gas, comprising:
  supplying the $CO_2$-containing gas to an absorber;
  supplying an aqueous absorption solution to the absorber;
  contacting the $CO_2$-containing gas with the aqueous absorption solution in the absorber to dissolve the $CO_2$ into the aqueous absorption solution, wherein:
    the aqueous absorption solution comprises a monovalent metal carbonate compound in a concentration between about 0.1 M and about 4 M; has a temperature between about 25° C. and about 80° C.; has an alkaline pH between about 9 and about 11.5 upon entering the absorber; and comprises a carbonic anhydrase polypeptide as defined in any one of implementations 1 to 7, free in solution in a concentration between about 0.05 g/L and about 4 g/L to catalyze the hydration reaction of the dissolved $CO_2$ into bicarbonate and hydrogen ions in the absorber, thereby producing an ion-rich solution the carbonic anhydrase polypeptide or functional derivative thereof and a $CO_2$-depleted gas;
  removing the ion-rich solution and the $CO_2$-depleted gas from the absorber;
  heating the ion-rich solution to produce a heated ion-rich solution having a stripping temperature;
  supplying the heated ion-rich solution to a stripper;
  converting bicarbonate and hydrogen ions into $CO_2$ gas and water, and producing a regenerated ion-depleted solution in the stripper, wherein:
    the stripper temperature is higher than the absorber temperature and is between about 30° C. and about 110° C.;
    the heated ion-rich solution has a pH in between about 8 and about 11 upon entering the stripper,
    the heated ion-rich solution has a $CO_2$ loading between about 0.05 and about 1 mol $CO_2$/mol monovalent cation;
  releasing the $CO_2$ gas from the stripper;
  releasing the regenerated ion-depleted solution from the stripper;
  cooling at least a portion of the ion-depleted solution to produce a cooled ion-depleted solution; and
  recycling at least a portion of the cooled regenerated ion-depleted solution back to the absorber to form at least part of the aqueous absorption solution.

15. The process of implementation 14, wherein said $CO_2$-containing gas comprises between about 5 vol % and about 50 vol % of $CO_2$.

16. The process of implementation 14 or 15, wherein said $CO_2$-containing gas further comprises CO, SOx, NOx compounds, $NH_3$, mercaptans, $H_2S$, $H_2$, heavy metals, dusts, ashes, or any combination thereof.

17. The process of any one of implementations 14 to 16, wherein said $CO_2$-containing gas is derived from natural gas combustion, coal combustion, biogas combustion, biogas upgrading, or natural gas sweetening.

18. The process of any one of implementations 14 to 17, wherein the absorber is a packed column.

19. The process of any one of implementations 14 to 18, wherein the monovalent metal carbonate is potassium carbonate.

20. The process of any one of implementations 14 to 18, wherein the monovalent metal carbonate is potassium carbonate is in a concentration between about 0.1 M and about 2 M, or between about 1.25 M and about 1.75 M.

21. The process of any one of implementations 14 to 20, wherein the temperature of the aqueous absorption solution in the absorber is between about 25° C. and about 70° C., preferably between about 30° C. and about 55° C.

22. The process of any one of implementations 14 to 21, wherein the pH of the aqueous absorption solution in the absorber is between about 9 and about 10.5, or between about 9.5 and about 10.5.

23. The process of any one of implementations 14 to 22, wherein substantially all of the cooled regenerated ion-depleted solution is recycled back to the absorber to form at least part of the aqueous absorption solution.

24. The process of any one of implementations 14 to 23, further comprising adding a make-up carbonic anhydrase polypeptide or functional derivative thereof component.

25. The process of implementation 24, wherein the make-up carbonic anhydrase polypeptide or functional derivative thereof component is added periodically.

26. The process of implementation 24, wherein the make-up carbonic anhydrase polypeptide or functional derivative thereof component is added continuously.

27. The process of any one of implementations 24 to 26, wherein the make-up carbonic anhydrase polypeptide or functional derivative thereof component comprises an amount of carbonic anhydrase polypeptide that corresponds to a deactivated amount of carbonic anhydrase polypeptide cycling between the absorber and the stripper.

28. The process of implementation 27, further comprising determining the deactivated amount of carbonic anhydrase polypeptide or functional derivative thereof, optionally the determining is done based on sampling and measurements of the aqueous absorption solution and/or the ion-rich solution, or on estimates and/or calculations from previously acquired experimental data, and/or based on overall process performance.

29. The process of any one of implementations 24 to 28, wherein the make-up carbonic anhydrase polypeptide or functional derivative thereof component is added into the aqueous absorption solution prior to entering the absorber.

30. The process of any one of implementations 14 to 29, wherein the absorber is a packed column or a rotating packed bed (RPB).

31. A method for absorbing $CO_2$ from a $CO_2$-containing gas, comprising:
    contacting the $CO_2$-containing gas with an aqueous absorption solution to dissolve the $CO_2$ into the aqueous absorption solution at commercial scale process conditions; and
    providing the carbonic anhydrase polypeptide as defined in any one of implementations 1 to 7 or functional derivative thereof, to catalyze the hydration reaction of the dissolved $CO_2$ into bicarbonate and hydrogen ions.

32. The method of implementation 31, further comprising providing operating conditions such that the carbonic anhydrase polypeptide or functional derivative thereof displays enhanced stability and/or activity compared to a reference enzyme.

33. The method of implementation 31 or 32, wherein the carbonic anhydrase polypeptide or functional derivative thereof provides an enhanced $CO_2$ flux of at least 8.5 times a corresponding $CO_2$ flux with no enzyme.

34. The method of any one of implementations 31 to 33, wherein the aqueous absorption solution comprises at least one absorption compound.

35. The method of implementation 34, wherein the at least one absorption compound comprises a primary amine, a secondary amine, a tertiary amine, a primary alkanolamine, a secondary alkanolamine, a tertiary alkanolamine, a primary amino acid, a secondary amino acid, a tertiary amino acid, dialkylether of polyalkylene glycols, dialkylether or dimethylether of polyethylene glycol, amino acid or a derivative thereof, monoethanolamine (MEA), 2-amino-2-methyl-1-propanol (AMP), 2-(2-aminoethylamino)ethanol (AEE), 2-amino-2-hydroxymethyl-1,3-propanediol (Tris or AHPD), N-methyldiethanolamine (MDEA), dimethylmonoethanol amine (DMMEA), diethylmonoethanolamine (DEMEA), triisopropanolamine (TIPA), triethanolamine (TEA), DEA, DIPA, MMEA, TIA, TBEE, HEP, AHPD, hindered diamine (HDA), bis-(tertiarybutylaminoethoxy)-ethane (BTEE), ethoxyethoxyethanol-tertiarybutyl amine (EEETB), bis-(tertiarybutylaminoethyl)ether, 1,2-bis-(tertiarybutylaminoethoxy)ethane and/or bis-(2-isopropylaminopropyl)ether, or any combination thereof.

36. The method of implementation 34, wherein the at least one absorption compound comprises a primary amine, a secondary amine, a tertiary amine, a primary alkanolamine, a secondary alkanolamine, a tertiary alkanolamine, a primary amino acid, a secondary amino acid, a tertiary amino acid, or any combination thereof.

37. The method of implementation 34, wherein the at least one absorption compound comprises dialkylether of polyalkylene glycols, dialkylether or dimethylether of polyethylene glycol, amino acid or derivative thereof or a combination thereof.

38. The method of implementation 34, wherein the at least one absorption compound comprises piperazine or derivative thereof, optionally the piperazine or derivatives thereof are substituted by at least one alkanol group.

39. The method of implementation 34, wherein the at least one absorption compound comprises monoethanolamine (MEA), 2-amino-2-methyl-1-propanol (AMP), 2-(2-aminoethylamino)ethanol (AEE), 2-amino-2-hydroxymethyl-1,3-propanediol (Tris or AHPD), N-methyldiethanolamine (MDEA), dimethylmonoethanolamine (DMMEA), diethylmonoethanolamine (DEMEA), triisopropanolamine (TIPA), triethanolamine (TEA), DEA, DTPA, MMEA, TIA, TBEE, HEP, AHPD, hindered diamine (HDA), bis-(tertiarybutylaminoethoxy)-ethane (BTEE), ethoxyethoxyethanol-tertiarybutylamine (EEETB), bis-(tertiarybutylaminoethyl)ether, 1,2-bis-(tertiarybutylaminoethoxy)ethane, and/or bis-(2-isopropylaminopropyl)ether.

40. The method of implementation 34, wherein the at least one absorption compound comprises an amino acid or derivative thereof.

41. The method of implementation 40, wherein the amino acid or derivative thereof comprises glycine, proline, arginine, histidine, lysine, aspartic acid, glutamic acid, methionine, serine, threonine, glutamine, cysteine, asparagine, valine, leucine, isoleucine, alanine, tyrosine, tryptophan, phenylalanine, taurine, N,cyclohexyl 1,3-propanediamine, N-secondary butyl glycine, N-methyl N-secondary butyl glycine, diethylglycine, dimethylglycine, sarcosine, methyl taurine, methyl-α-aminopropionicacid, N-(β-ethoxy)taurine, N-(β-aminoethyl)taurine, N-methyl alanine, 6-aminohexanoic acid, potassium or sodium salt of the amino acid, or any combination thereof.

42. The method of implementation 34, wherein the at least one absorption compound comprises a carbonate compound, preferably sodium carbonate, potassium carbonate or MDEA.

43. The method of implementation 34, wherein the at least one absorption compound comprises sodium carbonate.

44. The method of implementation 34, wherein the at least one absorption compound potassium carbonate.

45. The method of implementation 34, wherein the at least one absorption compound comprises a slow absorption compound.

46. The method of implementation 45, wherein said slow absorption compound comprises tertiary amines, tertiary alkanolamines, tertiary amino-acids, tertiary amino-acid salts, carbonates, or any mixture thereof.

47. The method of any one of implementation 31 to 46, wherein the carbonic anhydrase polypeptide is provided free in the absorption solution at a concentration sufficiently high to cause an increase in foaming of the absorption solution.

48. The method of implementation 47, wherein the absorption solution further comprises a defoamer, an anti-foam compound, or foam-reducer compound (e.g., an oil-in-water emulsion, a polyol based compound, a polyol based dispersion, a silicon based compound, a non-ionic silicon emulsion, and/or a silica particle suspension).

49. The method of implementation 48, wherein the defoamer, an anti-foam compound, or foam-reducer compound is provided in a concentration of at least 10 mg/L, at least 50 mg/L, at least 200 mg/L, between 50 and 300 mg/L, or between 100 and 300 mg/L, based on the volume of the absorption solution.

50. The method of any one of implementations 31 to 49, wherein the temperature of the absorption solution is at least 10° C., preferably at least 25° C.

51. The method of any one of implementations 31 to 50, wherein the step of contacting is performed at a temperature between about 10° C. and about 98° C., preferably between about 25° C. and about 80° C., more preferably between about 30° C. and about 70° C., more preferably between about 40° C. and about 50° C.

52. The method of any one of implementations 31 to 51, wherein the concentration of the carbonic anhydrase polypeptide or functional derivative thereof is between about 0.01 g/L and about 50 g/L in the absorption solution, optionally between about 0.3 g/L and about 10 g/L, optionally between about 0.3 g/L and about 4 g/L.

53. The method of any one of implementations 31 to 52, wherein the pH of the absorption solution is between about 8 and about 11.

54. The method of any one of implementations 31 to 53, wherein the $CO_2$ loading is between about 0.05 and about 1 mol $CO_2$/mol amine or mol $CO_2$/mol cation.

55. The method of any one of implementations 31 to 54, further comprising subjecting the ion-rich solution to desorption to produce a regenerated absorption solution and a $CO_2$ gas stream.

56. The method of any one of implementations 31 to 55, wherein the carbonic anhydrase polypeptide as defined in any one of implementations 1 to 7 or functional derivative thereof is a component of the absorption solution and the ion-rich solution and catalyzes the desorption reaction.

57. The method of any one of implementations 31 to 56, wherein the absorption is operated at a temperature between about 10° C. and about 98° C., optionally between about 25° C. and about 80° C., between about 30° C. and about 70° C., or between about 40° C. and about 50° C., optionally at 10° C., 20° C., 30° C., 40° C., 50° C., 60° C., 70° C., 80° C., 85° C., 90° C., 95° C. or 98° C. or any other value in between.

58. The method of any one of implementations 31 to 57, wherein the desorption is operated at a temperature between about 30° C. and about 110° C., optionally between about 35° C. and about 90° C. or between about 40° C. and about 70° C.

59. A method for $CO_2$ capture, comprising:
   in an absorption stage:
      contacting a $CO_2$-containing gas with an aqueous absorption solution to dissolve the $CO_2$ into the aqueous absorption solution;
      providing the carbonic anhydrase polypeptide as defined in any one of implementations 1 to 7 or functional derivative thereof in the absorption solution to catalyze the hydration reaction of the dissolved $CO_2$ into bicarbonate and hydrogen ions, thereby producing an ion-rich solution comprising at least some of the carbonic anhydrase polypeptide or functional derivative thereof and a $CO_2$-depleted gas; and/or
   in a desorption stage:
      providing conditions for treating the ion-rich solution comprising at least some of the carbonic anhydrase polypeptide or the functional derivative thereof, so as to desorb $CO_2$ gas from the ion-rich solution, thereby producing a regenerated absorption solution and a $CO_2$ gas stream.

60. The method of implementation 59, wherein the absorption stage is operated with the following absorption operating parameters:
   absorption temperature in between about 10° C. and about 98° C.;
   concentration of an absorption compound in the absorption solution between about 0.1 M and about 5 M;
   pH of the absorption solution in between about 8 and about 11; and/or
   $CO_2$ loading in between about 0.05 and about 1 mol $CO_2$/mol amine or mol $CO_2$/mol cation.

61. The method of implementation 59 or 60, wherein the desorption stage is operated with the following desorption operating parameter:
   desorption temperature in between about 30° C. and about 110° C.

62. The method of any one of implementations 59 to 61, wherein the absorption stage and desorption stage are operated within an overall operating temperature zone wherein the carbonic anhydrase polypeptide or functional derivative shows close to 100% residual activity after at least 1 week of exposure to overall operating temperature zone.

63. The method of any one of implementations 59 to 62, wherein the absorption stage and desorption stage are operated within an overall operating temperature zone wherein the carbonic anhydrase polypeptide or functional derivative provides enhanced temperature stability compared to a reference enzyme.

64. The method of implementation 63, further comprising one or more features as defined in any one of implementations 1 to 57.

65. A method for desorption of $CO_2$ from a solution comprising bicarbonate and hydrogen ions, comprising providing conditions desorption of the $CO_2$ in the presence of the carbonic anhydrase polypeptide as defined in any one of implementations 1 to 7 or functional derivative thereof, so as to catalyze the desorption of $CO_2$ gas from the solution, thereby producing an ion-depleted solution and a $CO_2$ gas stream.

66. The method of implementation 65, further comprising one or more features as defined in any one of implementations 1 to 64.

67. A system for absorbing $CO_2$ from a $CO_2$-containing gas, comprising:
    an absorption unit comprising:
        a gas inlet for receiving the $CO_2$-containing gas;
        a liquid inlet for receiving an aqueous absorption solution;
        a reaction chamber for contacting the $CO_2$-containing gas with the aqueous absorption solution to dissolve the $CO_2$ into the aqueous absorption solution, wherein the carbonic anhydrase polypeptide as defined in any one of implementations 1 to 7 or functional derivative thereof is present for catalyzing the hydration reaction of the dissolved $CO_2$ into bicarbonate and hydrogen ions, thereby producing an ion-rich solution and a $CO_2$-depleted gas;
        a liquid outlet for releasing the ion-rich solution; and
        a gas outlet for releasing the $CO_2$-depleted gas.

68. The system of implementation 67, further comprising a regeneration stage for regenerating the ion-rich solution.

69. The system of implementation 68, wherein the regeneration stage comprises a desorption unit and/or a mineralization unit 70. The system of any one of implementations 67 to 69, further comprising a temperature regulator for regulating the temperature of the absorption unit to promote enhanced stability of the carbonic anhydrase polypeptide or functional derivative thereof.

71. The system of any one of implementations 67 to 70, wherein the operating conditions are provided such that the combined stability and activity of the carbonic anhydrase polypeptide or functional derivative thereof provide enhanced overall $CO_2$ capture over time per given enzyme utilization.

72. The system of any one of implementations 67 to 71, further comprising a make-up device for providing a make-up carbonic anhydrase polypeptide or functional derivative thereof to system.

73. The system of implementation 72, wherein the make-up device comprises a make-up line in fluid communication with the system.

74. The system of implementation 73, wherein the make-up line is in fluid communication with the liquid inlet feeding into the absorption unit for adding the make-up carbonic anhydrase polypeptide or functional derivative thereof to the absorption solution.

75. The system of any one of implementations 67 to 74, further comprising a measurement device configured to measure a deactivation of the carbonic anhydrase polypeptide or functional derivative thereof in the system, optionally the measurement device is configured to retrieve a sample from the system, determine a sample activity of the carbonic anhydrase polypeptide or functional derivative thereof in the sample, compare the sample activity to an initial activity of the carbonic anhydrase polypeptide, and determine the deactivation of the carbonic anhydrase polypeptide or the functional derivative thereof.

76. The system of implementation 75, further comprising a controller coupled to the measurement device and the make-up device, the controller being configured to cause the make-up device to add an amount of the make-up carbonic anhydrase polypeptide or the functional derivative thereof based on the deactivation of the carbonic anhydrase polypeptide or the functional derivative thereof provided by the measurement device.

77. The system of any one of implementations 72 to 76, further comprising one or more features of any one of implementations 1 to 61.

78. An enzyme-enhanced $CO_2$ capture system, comprising:
    an absorption unit comprising:
        a gas inlet for receiving the $CO_2$-containing gas;
        a liquid inlet for receiving an aqueous absorption solution;
        a reaction chamber for contacting the $CO_2$-containing gas with the aqueous absorption solution to dissolve the $CO_2$ into the aqueous absorption solution;
        the carbonic anhydrase polypeptide as defined in any one of implementations 1 to 7 or functional derivative thereof that is present for catalyzing the hydration reaction of the dissolved $CO_2$ into bicarbonate and hydrogen ions, thereby producing an ion-rich solution and a $CO_2$-depleted gas;
        a liquid outlet for releasing the ion-rich solution; and
        a gas outlet for releasing the $CO_2$-depleted gas;
    a heat exchanger for heating the ion-rich solution to produce a heated ion-rich solution;
    a stripper unit comprising:
        a liquid inlet for receiving the ion-rich solution;
        a stripping chamber for allowing $CO_2$ to be released from the ion-rich solution to produce $CO_2$ gas stream and a regenerated solution, wherein the carbonic anhydrase polypeptide or functional derivative thereof is present for catalyzing the dehydration reaction;
        a liquid outlet for releasing the regenerated solution; and
        a gas outlet for releasing the $CO_2$ gas stream; and
    a recycle system for recycling at least a portion of the regenerated solution back to the liquid inlet of the absorption unit as at least part of the aqueous absorption solution.

79. The enzyme-enhanced $CO_2$ capture system of implementation 78, further comprising a make-up device for providing make-up carbonic anhydrase polypeptide or functional derivative thereof to the system.

80. The enzyme-enhanced $CO_2$ capture system of implementation 78 or 79, wherein the reaction chamber comprises packing material.

81. The enzyme-enhanced $CO_2$ capture system of any one of implementations 78 to 80, wherein the stripping chamber comprises packing material.

82. The enzyme-enhanced $CO_2$ capture system of any one of implementations 78 to 81, wherein the carbonic anhydrase polypeptide or functional derivative thereof is free in solution to cyclically flow between the absorption unit and the stripper unit 83. The enzyme-enhanced $CO_2$ capture system of any one of implementations 78 to 82, wherein the carbonic anhydrase polypeptide or the functional derivative thereof is immobilized on or in particles that are sized, configured and provided in a concentration so as to flow with the absorption solution and the regenerated solution, such that the particles cyclically flow between the absorption unit and the stripper unit.

84. The enzyme-enhanced $CO_2$ capture system of any one of implementations 78 to 83, wherein the $CO_2$-containing gas is biogas and/or raw petroleum gas.

85. The enzyme-enhanced $CO_2$ capture system of any one of implementations 78 to 84, wherein the $CO_2$-containing gas is pretreated by a separated unit to remove contaminants such as SOx, NOx and $H_2S$ before entering the absorber.

86. A commercial-scale enzyme-enhanced $CO_2$ capture facility configured to receive combustion gas comprising $CO_2$, generated by a combustion installation, the facility comprising:
- a feed line for supplying the combustion gas from the combustion installation;
- an absorption unit comprising:
  - a gas inlet for receiving the combustion gas;
  - a liquid inlet for receiving an aqueous absorption solution;
  - a reaction chamber for contacting the combustion gas with the aqueous absorption solution to dissolve the $CO_2$ into the aqueous absorption solution;
  - the carbonic anhydrase polypeptide as defined in any one of implementations 1 to 7 or functional derivative thereof that is present for catalyzing the hydration reaction of the dissolved $CO_2$ into bicarbonate and hydrogen ions, thereby producing an ion-rich solution and a $CO_2$-depleted combustion gas;
  - a liquid outlet for releasing the ion-rich solution; and
  - a gas outlet for releasing the $CO_2$-depleted combustion gas;
- a heat exchanger for heating the ion-rich solution to produce a heated ion-rich solution;
- a stripper unit comprising:
  - a liquid inlet for receiving the ion-rich solution;
  - a stripping chamber for allowing $CO_2$ to be released from the ion-rich solution to produce $CO_2$ gas stream and a regenerated solution, wherein carbonic anhydrase polypeptide or functional derivative thereof is present for catalyzing the dehydration reaction;
  - a liquid outlet for releasing the regenerated solution; and
  - a gas outlet for releasing the $CO_2$ gas stream; and
- a recycle system for recycling at least a portion of the regenerated solution back to the liquid inlet of the absorption unit as at least part of the aqueous absorption solution.

87. The facility of implementation 86, wherein the combustion gas generated by the combustion installation is from coal or natural gas combustion.

88. The facility of implementation 86 or 87, wherein the feed line and the absorption unit are configured such that the combustion gas is supplied to the absorption unit from the combustion installation without substantial pre-treatment to remove components from the combustion gas.

89. The facility of any one of implementations 86 to 88, further comprising one or more features as defined in any one of implementations 1 to 85.

In some implementations, any one of the methods, systems and/or facilities include one or more features as described above and/or as described in the present description. For instance, the methods, systems and/or facilities may include units, one or more absorption compounds; operating conditions such as temperature, pressure and concentration parameters or using a temperature swing or a pressure swing from absorption to desorption that is between certain temperature ranges described herein; one or more carbonic anhydrase polypeptide or functional derivatives thereof sequences as described herein; different types of $CO_2$-containing gases to treat; and so on.

BRIEF DESCRIPTION OF THE DRAWINGS

FIG. 1 shows the amino acid sequence of wild-type TACA (SEQ ID NO: 2) and its coding nucleic acid sequence (SEQ ID NO: 1). The N-terminal signal peptide (which is eventually cleaved) is underlined and may be replaced with a methionine. DNA sequence was taken from NCBI Reference Sequence: NC_014926.1.

FIG. 15 presents Table 4 summarizing the different variants identified by the directed evolution screening process. For all shown variants, the stability of a plurality of single mutations (i.e., containing only one amino acid substitution) and combinations of mutations in 1.45 M $K_2CO_3$ pH 10 at various temperatures, was compared to that of the TACA of SEQ ID NO: 7. Black boxes show variants with a half-life at least 150% that of SEQ ID NO: 7; double-boxes show variants with a half-life at least 125% that of SEQ ID NO: 7; single boxes show variants with a half-life less than 125% that of SEQ ID NO: 7, in at least one of the 3 test conditions of Table 3. Asterix indicates variants not characterized herein as a single mutant.

SEQUENCE LISTING

Figure 2:
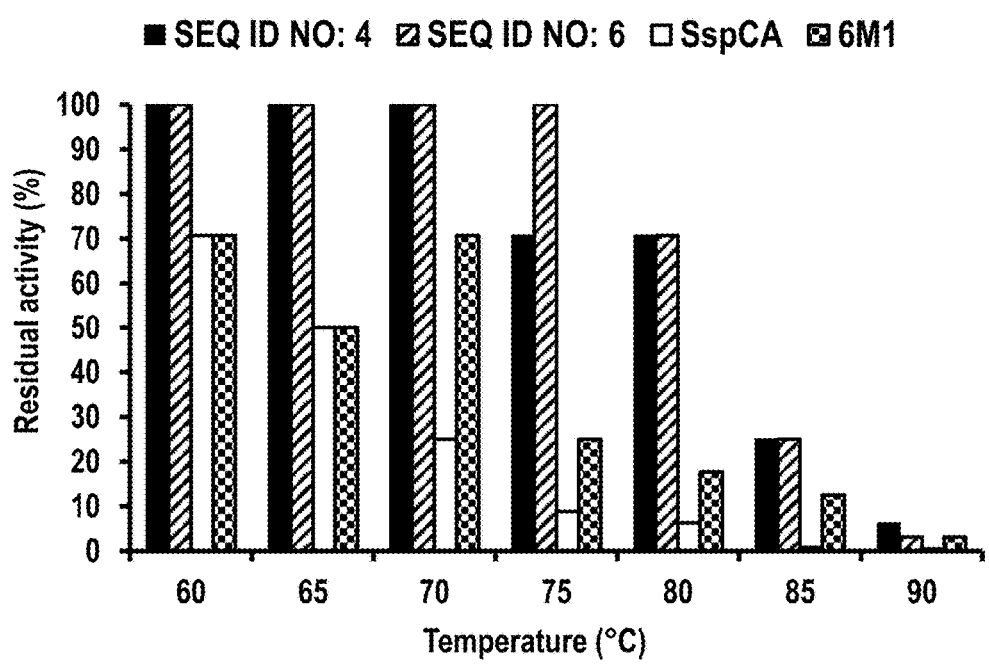
FIG. 2 is a graph of residual activity of various carbonic anhydrases, including TACA (SEQ ID NOs: 4 and 6), after 16 hours incubation in 1.45 M $KHCO_3/K_2CO_3$ pH 10 (2.9M $K^+$) at various temperatures.

This description contains a Sequence Listing in computer readable form entitled "Sequence_Listing.txr, created Sep. 1, 2016 having a size of about 20 kb. The computer readable form is incorporated herein by reference,

| SEQ ID NO: | Description |
|---|---|
| 1 | Nucleic acid sequence encoding SEQ ID NO: 2 (FIG. 1) |
| 2 | Amino acid sequence of wild-type TACA, including the 20-amino acid N-terminal signal sequence (FIG. 1) |
| 3 | Nucleic acid sequence encoding SEQ ID NO: 4 |
| 4 | Amino acid sequence of wild-type TACA, wherein the 20-amino acid N-terminal signal sequence of the wild-type TACA is replaced with a methionine residue. |
| 5 | Nucleic acid sequence encoding SEQ ID NO: 6/7 |
| 6/7 | Amino acid sequence of an N-terminal truncated wild-type TACA variant displaying higher expression in a bacterial host, wherein the first six amino acids of SEQ ID NO: 4 ("MGGGAH") are replaced with the four residues "MEHE", giving the TACA enzyme of SEQ ID NO: 6/7. SEQ ID NOs: 6 and 7 refer to the same protein. |
| 8 | Amino acid sequence of carbonic anhydrase from *Sulfurihydrogenibium* sp. ("SspCA"). |
| 9 | Amino acid sequence of a thermostable variant of SspCA referred to as "6M1". |
| 10 | Amino acid sequence of wild-type TACA beginning at the highly conserved tryptophan residue at position 26 of SEQ ID NO: 2, position 7 of SEQ ID NO: 4, or position 5 of SEQ ID NO: 6 or 7. |

DETAILED DESCRIPTION

Various methods and/or techniques are provided herein for $CO_2$ capture using a TACA or functional derivative thereof for catalysis, leveraging the stability and activity of the TACA or functional derivative thereof for operating conditions of the $CO_2$ capture process.

TACA is a carbonic anhydrase that catalyzes the interconversion of $CO_2$ and water to bicarbonate and hydrogen ions. TACA is obtained or derived from the thermophilic bacteria *Thermovibrio ammonificans* (TA) (Giovannelli D, Ricci J, Pérez-Rodriguez I, Hügler M, O'Brien C, Keddis R, Grosche A, Goodwin L, Bruce D, Davenport K W, Dotter C, Han J, Han S, Ivanova N, Land M L, Mikhailova N, Nolan M, Pitluck S, Tapia R, Woyke T, Vetriani C. "Complete genome sequence of *Thermovibrio ammonificans* HB-1(T), a thermophilic, chemolithoautotrophic bacterium isolated from a deep-sea hydrothermal vent" Standards in Genomic Science 2012 7:82-90.). Methods for isolating/obtaining an enzyme from bacteria are known, such as immunoprecipitation, ultracentrifugation or chromatographic methods. Further details and definitions related to TACA may be found in the Definitions section below. TA grows in the temperature range of 60° C. to 80° C. and optimally at a pH of 5.5.

So far, biochemical study on TACA has been limited. TACA has been the subject of PCT/KR2014/004328. Jo B H, Seo J H, Cha H J, *Bacterial extremo-α-carbonic anhydrases from deep-sea hydrothermal vents as potential biocatalysts for $CO_2$ sequestration*. Journal of Molecular Catalysis B: Enzymatic. 2014, November; 109: p. 31-39 (hereafter "Jo et al.") and James P, Isupov M N, Sayer C, Saneei V, Berg S, Lioliou M, Kotlar H K, Littlechild J A. *The structure of a tetrameric α-carbonic anhydrase from Thermovibrio ammonificans reveals a core formed around intermolecular disulfides that contribute to its thermostability*. Acta Crystallogr D Biol Crystallogr. 2014, October; 70 (Pt 10):2607-18 (hereafter "James et al."), describe preliminary assessment of TACA relative to other known CA enzymes. These works test and assess TACA in relatively mild conditions, such as low-concentrated buffer (pH of about 8) and low ionic strength. However, relatively different process conditions are present in real industrial $CO_2$ capture applications, which may include conditions such as high pH (e.g., 9 to 11), thermal cycling (temperature swings ranging from 25° C. to 105° C., for example, when cycling from absorption to stripping), very high ionic strength, shear forces, turbulence, and large gas-liquid interfaces which promote mass transfer (yet can have denaturing effects). In addition, due to the relatively high concentrations of carbonate ions contained in various $CO_2$ capture solvents, proteins can face solubility issues, as reported for example in Yanjie Zhang and Paul S. Cremer. *Chemistry of Hofmeister Anions and Osmolytes*. Annu Rev Phys Chem. 2010. 61:63-83 (hereafter "Zhang & Cremer") which describes that the carbonate ion can be a highly efficient protein precipitator.

In addition, neither Jo et al. nor James et al. studied wild type TACA. Jo et al. studied TACA with an extra six histidines tag at the C-terminal end. As shown in the 3D structure of TACA described by James et al., TACA's carboxy terminal functional group is implied in the adoption of a tetrameric organisation. Jo et al. suggest that TACA is a dimeric enzyme while James et al. describe TACA as a tetramer. Moreover, James et al. report that TACA properties can greatly differ according to its oligomerisation state. In James et al., the TACA enzyme which was studied had at its N-terminal end a six histidines tag plus the 20-residues secretion signal. The N-terminal region being close to the active site, significant changes in stability and activity may have occurred.

As will be described further below, signification work, development and testing have been conducted and found that TACA and functional derivatives thereof are operable in the industrial process conditions of a $CO_2$ capture operation and can provide even greater temperature stability than reported in the literature.

TACA also provides enhanced performance of enzyme-assisted $CO_2$ capture compared to other CAs, such as *Sulfurihydrogenibium* sp. (Ssp) CA. Like TA, the bacteria Ssp belongs to the Aquificales order. Ssp was isolated from the Calcite Hot Springs in Yellowstone National Park (USA) and like TA, grows in 60° C. to 80° C. temperature range. *Sulfurihydrogenibium yellowsfonense* sp. nov. is an extremely thermophilic, facultatively heterotrophic, sulfur-oxidizing bacterium from Yellowstone National Park. This bacteria along with *Sulfurihydrogenibium subterraneum* and *Sulfurihydrogenibium azorense* are described in Nakagawa S, Shtaih Z, Banta A, Beveridge T J, Sako Y, Reysenbach A L. International Journal of Systematic and Evolutionary Microbiology, 2005 November; 55(Pt 6):2263-8. (PubMed ID 16280480).

Distinctly, Ssp grows optimally at pH 7.5, a value two orders of magnitude higher than that of TA. Ssp genome contains a gene encoding for an alpha-class carbonic anhydrase hereafter referred as SspCA. Some recent biochemical characterizations of SspCA are reported in the literature. However, it is hard to expect or predict TACA properties based on those of SspCA, given that the two proteins share only 49% sequence identity.

Both SspCA and TACA are believed to be secreted after being produced because of the presence of a signal peptide. In that context, TACA and SspCA have to deal with conditions occurring outside the bacteria. Because of the different optimal growth pH of Ssp vs TA, one could expect SspCA to be more robust than TACA when dissolved in $CO_2$ capture solvents, the latter being alkaline with pH ranging from 8 to 11. However, embodiments of the present description provide results revealing that TACA stability is surprisingly much higher than that of SspCA in tested relevant $CO_2$ capture solvents and conditions.

Referring to FIG. 1, an amino acid sequence of a TACA is illustrated. The cleaved signal peptide is underscored and may be replaced with a methionine (SEQ ID NO: 4). Various TACA variants and functional derivatives may also be used in the $CO_2$ capture techniques described herein. For example, the first six amino acids of the TACA of SEQ ID NO: 4 ("MGGGAH") were replaced by four other amino acids ("MEHE"), giving the TACA of SEQ ID NO: 6/7. This change was performed in order to increase enzyme production level and did not have a measureable negative impact on TACA stability (FIGS. 2 to 5). Table 3 describes many other stabilized variants from SEQ ID NO: 7 that were constructed using directed evolution approaches.

Figure 10:
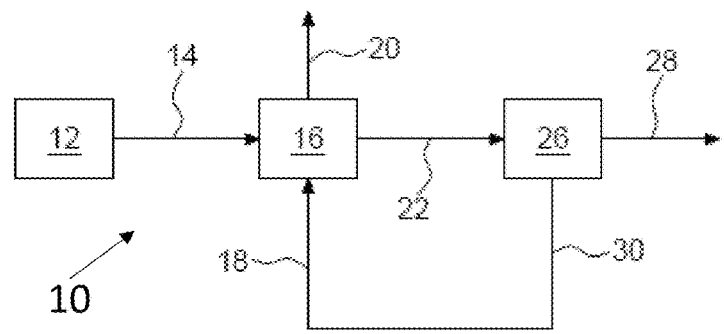
FIG. 10 is a process flow diagram illustrating one embodiment, using a $CO_2$ capture system.

Referring now to FIG. 10, an example of the overall $CO_2$ capture system 10 includes a source 12 of $CO_2$ containing gas 14. The source may be a power plant, an aluminum smelter, refinery or another type of $CO_2$ producing operation at high or atmospheric pressure, or may also be ambient air for some specific applications such as air fractionation, air cleaning, or biogas. The $CO_2$ containing gas 14 is supplied to an absorption unit 16, which is also fed with an aqueous absorption solution 18 for contacting the $CO_2$ containing gas 14. In some implementations, the aqueous absorption solution 18 includes a carbonic anhydrase which is TACA or a functional derivative thereof and an absorption compound. The carbonic anhydrase may be free in the aqueous absorption solution 18 as dissolved enzyme or aggregates or particles of enzymes. The carbonic anhydrase may be on or in particles that are present in the aqueous absorption solution 18 and flow with it through the absorption unit 16. The carbonic anhydrase may be immobilized with respect to the particles using any method while keeping at least some of its activity. Some immobilization techniques include covalent bonding, entrapment, encapsulation, and so on. The carbonic anhydrase may be immobilized with respect to supports, which may be various structures such as packing material, within the absorption unit 16 so as to remain within the absorption unit 16 as the aqueous absorption solution 18 flows through it.

The $CO_2$ containing gas 14 may be a $CO_2$-containing effluent from various sources that includes a proportion of $CO_2$ and other gases. For example the gas may include from about 0.03% to 60% (v/v) of $CO_2$ although the $CO_2$ concentration may be greater. The $CO_2$-containing gas may also be a gas having high $CO_2$ content up to 100%, which may be useful for the production of compounds such as sodium bicarbonate from $CO_2$ gas as one of the starting materials.

The absorption unit 16 (also referred to as an "absorber" herein) may be of various types, such as a packed reactor, a spray reactor, a bubble column type reactor, a rotating packed bed (RPB) or other type of process intensification (PI) reactor, and so on. There may be one or more reactors that may be provided in series or in parallel. In the absorption unit 16, the TACA or functional derivative thereof catalyses the hydration reaction of $CO_2$ into bicarbonate and hydrogen ions and thus a $CO_2$ depleted gas 20 and an ion-rich solution 22 are produced.

The ion-rich solution 22 is then supplied to a desorption unit 26 (also referred to herein as a "stripper") to produce a $CO_2$ stream 28 and an ion depleted solution 30. The TACA or functional derivative thereof may also be present to catalyse the dehydration reaction of bicarbonate ions into $CO_2$ and thus a $CO_2$ depleted gas 20 and an ion depleted solution 30 is produced. Alternatively, the ion-rich solution 22 may be supplied to another type of regeneration step such as mineral carbonation and the like. It should be noted that the ion-rich solution 22 may be heated prior to being supplied to the desorption unit 26.

Figure 11:
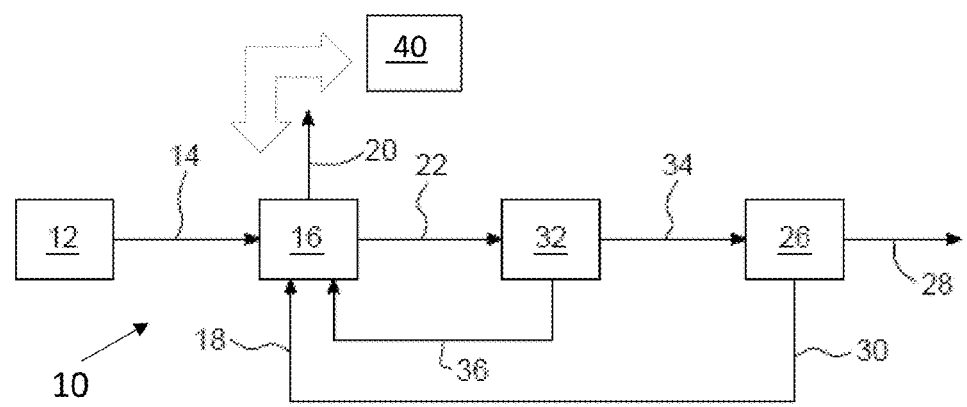
FIG. 11 is another process flow diagram illustrating one embodiment, using a $CO_2$ capture system including a separation unit.
Figure 12:
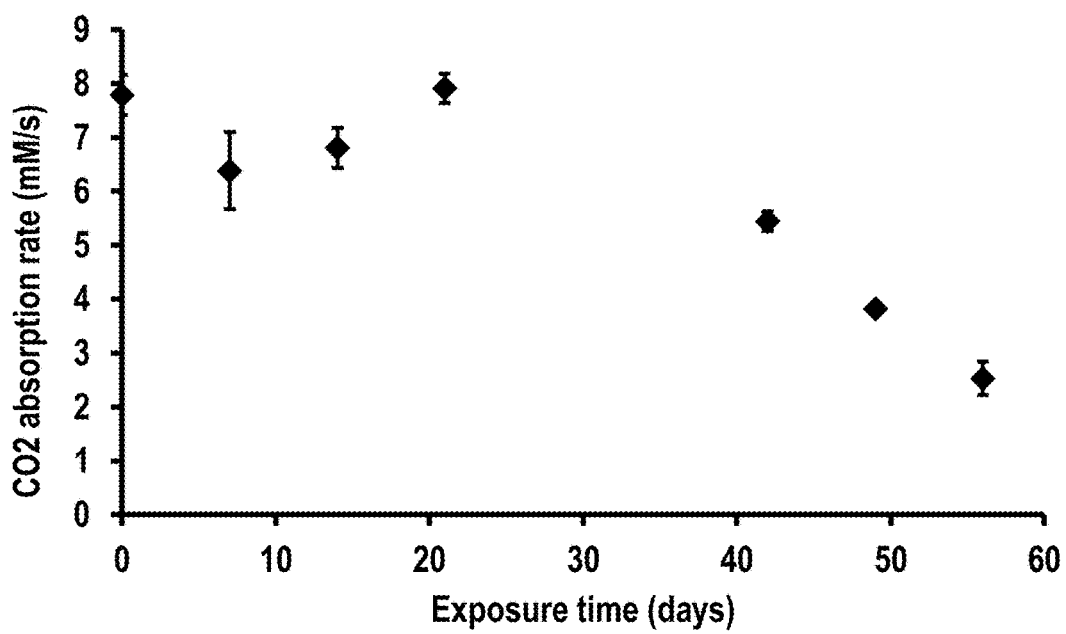
FIG. 12 shows the residual activity of TACA over time when continuously exposed to a 1.45 M $K_2CO_3$ pH 10 solution under temperature cycling conditions.
Figure 13:
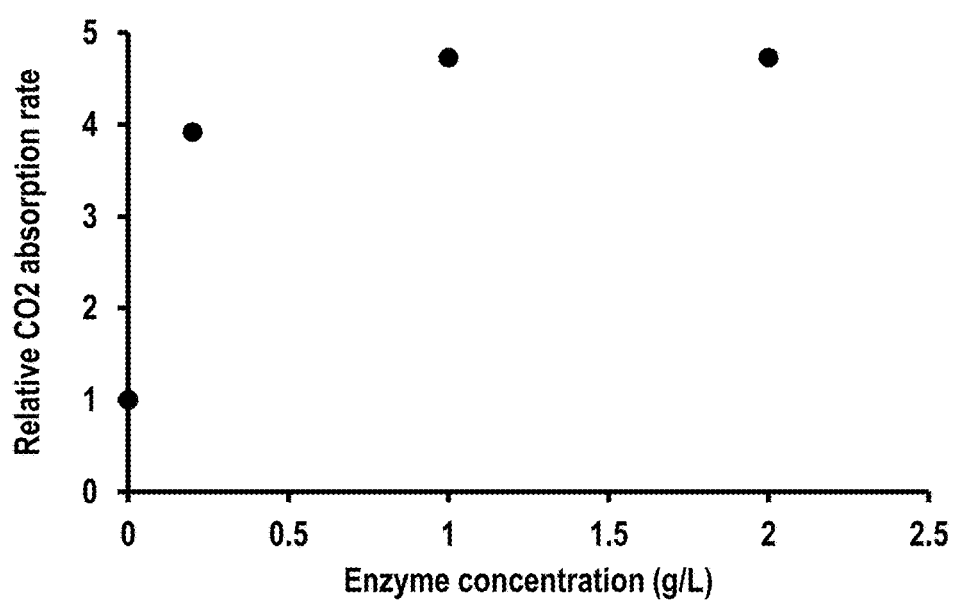
FIG. 13 is a graph showing relative $CO_2$ absorption rate versus enzyme concentration illustrating the impact of adding TACA to a 1.45 M $K_2CO_3$ solution at different concentrations on the $CO_2$ absorption rate of the 1 ton per day $CO_2$ capture unit.

Referring now to FIG. 11, the system 10 may also include a separation unit 32 arranged in between the absorption unit 16 and the desorption unit 26, for removing at least some and possibly all of the TACA or functional derivative thereof in the event the enzyme is flowing with the ion-rich solution 22, e.g. when the enzyme is free in solution or immobilized with respect to flowing particles. The separation unit 32 produces an enzyme depleted stream 34 that may be supplied to the desorption unit 26 and an enzyme rich stream 36 that may be recycled, in whole or in part, to the absorption unit 16. The separation unit may also include one or more separators in series or parallel. The separators may be filters or other types of separators, depending on the removal characteristics for the enzymes and the form of the enzymes or particles.

The system may also include various other treatment units for preparing the ion-rich solution 22 for the desorption unit 26 and/or for preparing the ion depleted solution 30 for recycling into the absorption unit 16. There may be pH adjustment units or various monitoring units.

In some implementations, at least one TACA or functional derivative thereof is provided in the desorption unit 26. The TACA or functional derivative thereof may be provided within the input ion-rich solution and/or added separately. The TACA or functional derivative thereof may be tailored, designed, immobilised or otherwise delivered in order to withstand the conditions in the desorption unit 26. The TACA or the functional derivative thereof may catalyze the conversion of bicarbonate ion to $CO_2$ as described in Reaction 1 (reverse reaction).

Referring still to FIG. 11, the system may also include a measurement device 40 for monitoring properties of various streams and adjusting operation of the absorption unit 16 to achieve desired properties. Adjusting could be done by various methods including modifying the liquid and/or gas flow rates, for example, or adjusting other operating conditions. In some implementations, the measurement device 40 can monitor the activity of the TACA or the functional derivative thereof cycled through the $CO_2$ capture system 10, and this information can be used to determine, calibrate and/or control the addition of the make-up TACA or functional derivative thereof into the system.

In some implementations, the absorption unit 16 may be operated at conditions so as to leverage the activity and/or stability of the TACA or functional derivative thereof used to catalyze the $CO_2$ hydration reaction. For example, it has been found that TACA or the functional derivative thereof can present high residual activity over a range of elevated temperatures in aqueous absorption solutions including sodium carbonate or potassium carbonate. The TACA or functional derivative thereof also presents high activity at lower ambient temperature to provide elevated $CO_2$ flux in aqueous absorption solutions including sodium carbonate, potassium carbonate or alkanolamines such as MDEA. The operating conditions may include an operating temperature and at least one operating absorption compound within the absorption solution. The operating conditions may further include pH, $CO_2$ loading, gas and liquid flow rates and compositions, and so on.

In some implementations, the operating conditions are coordinated for maximum leverage of the TACA or functional derivative thereof functionality in $CO_2$ capture. In some implementations, the operating conditions are provided for commercial scale $CO_2$ capture operations—such as relatively high pH, high ionic strength, high temperature, and so on—and the TACA or functional derivative or variant thereof provides high performance for catalysis of the desired reaction(s) in the cyclic system.

In some implementations, the operating conditions may include temperature conditions that, depending on various other parameters of the $CO_2$ capture operation, may provide an absorption temperature higher than 10° C. and lower than 98° C., such as between 25 and 80° C., 30 and 70° C. or 30 and 50° C. or such as 15° C., 20° C., 25° C., 30° C., 35° C., 40° C., 45° C., 50° C., 55° C., 60° C., 65° C., 70° C., 75° C., 80° C., 85° C., 90° C., 95° C., 98° C., or any temperature in between. It should also be understood that the temperature conditions in the absorption unit may vary within a certain temperature range, since the operating temperatures at different locations within the absorption unit will be different. In addition, the temperature of the absorption solution can substantially fluctuate throughout absorption and desorption stages that can be used in some $CO_2$ capture operations.

In some implementations, the operating conditions may include pressure conditions that, depending on various other parameters of the $CO_2$ capture operation, may provide an absorption pressure higher than 1 bar and lower than 100 bar, such as 2 bars, 5 bars, 10 bars, 20 bars, 25 bars, 30 bars, 35 bars, 40 bars, 45 bars, 50 bars, 55 bars, 60 bars, 65 bars, 70 bars, 75 bars, 80 bars, 85 bars, 90 bars, 95 bars, 100 bars, or any pressure in between.

In some implementations, the operating conditions may include temperature conditions that, depending on various other parameters of the $CO_2$ capture operation, may provide a desorption temperature higher than 10° C. and lower than 110° C., such as between 30 and 110° C., 35 and 90° C. or 40 and 70° C. or such as 15° C., 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C. or any temperature in between. It should also be understood that the temperature conditions in the desorption unit may vary within a certain temperature range, since the operating temperatures at different locations within the desorption unit will be different. In addition, the temperature of the absorption solution can substantially fluctuate throughout absorption and desorption stages that can be used in some $CO_2$ capture operations. It should also be noted that the operating conditions may include a temperature swing between the absorption unit and the desorption unit, and the temperature swing may vary between about 25° C. and about 105° C., optionally between about 30° C. and about 85° C., or between about 40° C. and about 60° C., for example. Different temperature swings can be used depending on various operating parameters, such as type of solvent or absorption compound(s) used in the process.

In some implementations, the operating conditions may include pressure conditions that, depending on various other parameters of the $CO_2$ capture operation, may provide a desorption absolute pressure higher than 0.05 bar and lower than 50 bars, such as 0.1 bar, 0.2 bars, 0.3 bar, 0.4 bar, 0.5 bar, 0.6 bar, 0.7 bar, 0.8 bar, 0.9 bar, 1 bar, 2 bars, 5 bars, 10 bars, 15 bars, 20 bars, 25 bars, 30 bars, 35 bars, 40 bars, 45 bars, 50 bars or any absolute pressure in between.

In some implementations, the operating conditions may include an aqueous absorption solution including an absorption compound, which will be further discussed below.

The enzyme is preferably used in combination with an absorption solution that will supply the $CO_2$ carrying capacity for the process. The solution may have a composition allowing acceleration of the enzyme catalytic rate by capturing the hydrogen ion released during the hydration reaction. Using TACA or a functional derivative thereof allows the $CO_2$ capture operation to be accelerated, reducing the size of the required capture vessels and associated capital costs. In addition, by taking advantage of this accelerative mechanism, energetically favorable absorption compounds such as tertiary and hindered amines, carbonate/bicarbonate solutions and amino acids/amino acid salts can be employed to reduce associated process energy consumption, where these absorption compounds would normally be too slow to be used efficiently without enzymatic catalysis.

The aqueous absorption solution may include at least one absorption compound that aids in the absorption of $CO_2$. The absorption compound may include potassium carbonate, sodium carbonate, ammonium carbonate, and/or at least one amine, which may be a primary amine, a secondary amine, a tertiary amine, a primary alkanolamine, a secondary alkanolamine, a tertiary alkanolamine, and/or an amino acid with primary, secondary or tertiary amino group(s) or a combination thereof. Combinations of absorption compounds include a carbonate and at least one of the amines and/or amino acids mentioned therein or herein, to produce a promoted carbonate absorption solution. It should also be noted that the absorption solution can include a single absorption compound, such as potassium carbonate. In addition, the absorption solution can include a main absorption compound, such as potassium carbonate, and also one or more secondary compounds that may include an amine, for example.

In some scenarios, the absorption compound may include monoethanolamine (MEA), 2-amino-2-methyl-1-propanol (AMP), 2-(2-aminoethylamino)ethanol (AEE), 2-amino-2-hydroxymethyl-1,3-propanediol (Tris or AHPD), N-methyldiethanolamine (MDEA), dimethylmonoethanolamine (DMMEA), diethylmonoethanolamine (DEMEA), triisopropanolamine (TIPA), triethanolamine (TEA), DEA, DIPA, MMEA, TIA, TBEE, HEP, AHPD, hindered diamine (HDA), bis-(tertiarybutylaminoethoxy)-ethane (BTEE), ethoxyethoxyethanol-tertiarybutylamine (EEETB), bis-(tertiarybutylaminoethyl)ether, 1,2-bis-(tertiarybutylaminoethoxy)ethane and/or bis-(2-isopropylaminopropyl)ether, and the like.

In some scenarios, the absorption compound may include piperidine, piperazine, derivatives of piperidine, piperazine which are substituted by at least one alkanol group, dialkylether of polyalkylene glycols, dialkylether or dimethylether of polyethylene glycol, amino acids comprising glycine, proline, arginine, histidine, lysine, aspartic acid, glutamic acid, methionine, serine, threonine, glutamine, cysteine, asparagine, valine, leucine, isoleucine, alanine, tyrosine, tryptophan, phenylalanine, and derivatives such as taurine, N,cyclohexyl 1,3-propanediamine, N-secondary butyl glycine, N-methyl N-secondary butyl glycine, diethylglycine, dimethylglycine, sarcosine, methyl taurine, methyl-α-aminopropionic acid, N-(β-ethoxy)taurine, N-(β-aminoethyl)taurine, N-methyl alanine, 6-aminohexanoic acid, potassium or sodium salt of the amino acid or a combination thereof.

The absorption compound used to make up the aqueous absorption solution may be at least one of the example compounds, i.e. potassium carbonate, sodium carbonate and/or MDEA.

In some scenarios, the concentration of the absorption compound in the solution may be between about 0.1 M and about 10 M, depending on various factors. When the absorption compound is amine-based, the concentration of the amine-based solution may be between about 0.1 M and 8 M and when the absorption compound is amino acid-based, the concentration of the amino acid-based solution may be between about 0.1 M and 6 M. When the absorption compound is carbonate based, the pH of the absorption solution may be between about 8 and about 12, depending for example on the absorption compound and on the $CO_2$ loading of the solution.

The TACA or functional derivative thereof may be dissolved in the absorption solution. The concentration of the TACA or functional derivative thereof may be between about 0.01 and about 50 g/L, between about 0.01 and about 10 g/L or between about 0.1 and about 5 g/L. When the TACA or functional derivative thereof is not dissolved in the solution but is rather immobilized on mobile particles or fixed on packing material, the amount of immobilized TACA or functional derivative thereof may be similar so as to provide a similar activity as the therein mentioned concentrations of dissolved TACA or functional derivative thereof.

As noted above, the TACA or functional derivative thereof may be provided free or dissolved in the solvent, immobilized or entrapped or otherwise attached to particles that are in the absorption solution or to packing material or other structures that are fixed within the reaction chamber.

In the case where the TACA or functional derivative thereof is immobilized with respect to a support material, this may be accomplished by an immobilization technique selected from adsorption, covalent bonding, entrapment, copolymerization, cross-linking, and encapsulation, or combination thereof.

In one scenario, the TACA or functional derivative thereof may be immobilized on a support that is in the form of particles, beads or packing. Such supports may be solid or porous with or without coating(s) on their surface. The TACA or functional derivative thereof may be covalently attached to the support and/or the coating of the support, or entrapped inside the support or the coating. The coating may be a porous material that entraps the TACA or functional derivative thereof within pores and/or immobilizes the TACA by covalent bonding to the surfaces of the support. The support material may be made from a compound different than the TACA or functional derivative thereof. The support material may include nylon, cellulose, silica, silica gel, chitosan, polyacrylamide, polyurethane, alginate, polystyrene, polymethylmetacrylate, magnetic material, sepharose, titanium dioxide, zirconium dioxide and/or alumina, respective derivatives thereof, and/or other materials. The support material may have a density between about 0.6 g/ml and about 5 g/ml such as a density above 1 g/ml, a density above 2 g/mL, a density above 3 g/mL or a density of about 4 g/mL.

In some scenarios, the TACA or functional derivative thereof may be provided as cross-linked enzyme aggregates (CLEAs) and/or as cross-linked enzyme crystals (CLECs).

In the case of using enzymatic TACA or functional derivative thereof particles, including CLEAs or CLECs, the particles may be sized to have a diameter at or below about 17 µm, optionally about 10 µm, about 5 µm, about 4 µm, about 3 µm, about 2 µm, about 1 µm, about 0.9 µm, about 0.8 µm, about 0.7 µm, about 0.6 µm, about 0.5 µm, about 0.4 µm, about 0.3 µm, about 0.2 µm, about 0.1 µm, about 0.05 µm, or about 0.025 µm. The particles may also have a distribution of different sizes.

The TACA or functional derivative thereof used in connection with the techniques described herein may be an isolated and/or substantially pure form.

There is also provided a carbonic anhydrase polypeptide or functional derivatives thereof, which is stable and active at a broad range of temperatures.

In one implementation, the carbonic anhydrase is a polypeptide comprising the sequence as set forth in SEQ ID NO: 2, 4, 6 or 7 or functional derivative thereof, an expression or cloning vector comprising a nucleotide sequence encoding such carbonic anhydrase, and a transgenic cell comprising such expression or cloning vector.

The TACA or the derivative thereof can be used in various processes and scenarios such as those described in the following patent references that are hereby incorporated herein by reference: CA 2,291,785; CA 2,329,113; CA 2,393,016; CA 2,443,222; U.S. Pat. No. 6,908,507; EP 1 377 531, U.S. Pat. Nos. 7,514,056; 7,596,952; 8,066,965; 8,277,769; 6,946,288; 7,740,689; WO2012/103653; US 2013/0203155; CA 2,769,771; US 2012/0122195; U.S. Pat. No. 8,722,391; CA 2,554,395; CA 2,738,061; WO2014/066999; CA 2,886,708.

DEFINITIONS

In order to further appreciate some of the terms used herein, the following definitions and discussion are provided.

The term "a" or "the" refers to "at least one" and can cover "several".

The expression "polypeptide" refers to any peptide or protein comprising two or more amino acids joined to each other by peptide bonds or modified peptide bonds. "Polypeptide(s)" refers to both short chains, commonly referred to as peptides, oligopeptides and oligomers, and to longer chains generally referred to as proteins. Polypeptides may contain amino acids other than the 20 gene-encoded amino acids, optionally polypeptides may contain glycine, proline, arginine, histidine, lysine, aspartic acid, glutamic acid, methionine, serine, threonine, glutamine, cysteine, asparagine, valine, leucine, isoleucine, alanine, tyrosine, tryptophan, phenylalanine, selenocysteine, selenomethionine, pyrrolysine. "Polypeptide(s)" include those modified either by natural processes, such as processing and other post-translational modifications, but also by chemical modification techniques. Such modifications are well described in basic texts and in more detailed monographs, as well as in a voluminous research literature and they are well known to those of skill in the art. It will be appreciated that the same type of modification may be present in the same or varying degree at several sites in a given polypeptide.

The expression "functional derivative" refers to a protein/peptide/polypeptide sequence that possesses a functional biological activity that is substantially similar to the biological activity of the original protein/peptide/polypeptide sequence. In other words, it refers to a polypeptide of the carbonic anhydrase as defined herein that substantially retain(s) the capacity of catalyzing the hydration of carbon dioxide. In this description, the term "TACA" includes its functional derivatives, which have carbonic anhydrase activity. A functional derivative of the carbonic anhydrase protein/peptide as defined herein may or may not contain post-translational modifications such as covalently linked carbohydrates, if such modifications are not necessary for the performance of a specific function. The "functional derivative" may also comprise nucleic acid sequence variants encoding the protein/peptide/polypeptide of the present description. These variants may result from the degeneracy of the genetic code or from a mutation, substitution, addition or deletion. Further, the carbonic anhydrase as defined herein may comprise a Tag such as a histidine Tag. The term "functional derivative" is meant to encompass the "variants", the "mutants", the "fragments" or the "chemical derivatives" of a carbonic anhydrase protein/peptide. Methods for measuring carbonic anhydrase activity are known such as stirred cell reactor assay or the method described by Chirica et al. (Chirica et al. European Journal of Biochemistry, 1997, 244, 755-60). These functional derivatives have at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% 99% or 99.5% identity with the sequence as set forth in SEQ ID NO: 2, 4, 6, 7, or 10 optionally over the entire length of the sequence or on a partial alignment of the sequences.

The term "polynucleotide fragment", as used herein, refers to a polynucleotide whose sequence (e.g., cDNA) is an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art.

The term "polypeptide or fragments thereof" as used herein refers to peptides, oligopeptides and proteins. This term also does not exclude post-expression modification of polypeptides. For example, polypeptides that include the covalent attachment of glycosyl groups, acetyl groups, lipid groups and the like are encompassed by the term polypeptide.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Another method of establishing percent identity which can be used in the context of the present description is the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

As used herein, the phrase "at a position corresponding to the position of and similar phrases, refer to the fact that a person of skill in the art would be able to perform for example a multiple sequence alignment of one or more proteins of a given family (e.g., carbonic anhydrases) to determine whether two amino acids in two different proteins of different lengths and/or residue numbering correspond to the same position within the secondary or tertiary structure of the protein.

By "substantially identical" when referring to a polypeptide, it will be understood that the polypeptide of the present description preferably has an amino acid sequence having at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or any other value in between to SEQ ID NO: 2, 4, 6, 7 or 10, or functional derivatives thereof, optionally over the entire length of the peptide.

One can use a program such as the CLUSTAL program to compare amino acid sequences. This program compares amino acid sequences and finds the optimal alignment by inserting spaces in either sequence as appropriate. It is possible to calculate amino acid identity or homology for an optimal alignment. A program like BLASTp will align the longest stretch of similar sequences and assign a value to the fit. It is thus possible to obtain a comparison where several regions of similarity are found, each having a different score. Both types of identity analysis are contemplated for the present description.

With respect to protein or polypeptide, the term "isolated polypeptide" or "isolated and purified polypeptide" is sometimes used herein. This term refers primarily to a protein produced by expression of an isolated and modified polynucleotide molecule contemplated by the present description. Alternatively, this term may refer to a protein which has been sufficiently separated from other proteins with which it would naturally be associated, so as to exist in "substantially pure" form.

The term "substantially pure" refers to a preparation comprising at least 50% by weight of the carbonic anhydrase polypeptide or derivative thereof on total protein content. More preferably, the preparation comprises at least 75% by weight, and most preferably 90-99% by weight, of the carbonic anhydrase polypeptide or derivative thereof.

Purity is measured by methods appropriate for the carbonic anhydrase polypeptide or derivative thereof as described herein (e.g. chromatographic methods, agarose or polyacrylamide gel electrophoresis, HPLC analysis, and the like).

The TACA polypeptide or TACA functional derivative thereof can also comprise amino acids substitution such that the carbonic anhydrase or TACA functional derivative thereof retains catalytic activity (i.e. the interconversion of $CO_2$ with $HCO_3$ and $H^+$). The term "substituted amino acid" is intended to include natural amino acids and non-natural amino acids. Non-natural amino acids include amino acid derivatives, analogues and mimetics. As used herein, a "derivative" of an amino acid refers to a form of the amino acid in which one or more reactive groups on the compound have been derivatized with a substituent group. As used herein an "analogue" of an amino acid refers to a compound that retains chemical structures of the amino acid necessary for functional activity of the amino acid yet also contains certain chemical structures that differ from the amino acid. As used herein, a "mimetic" of an amino acid refers to a compound that mimics the chemical conformation of the amino acid.

As used herein, the term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, cDNA, single- and double-stranded RNA, and RNA that is a mixture of single- and double-stranded regions, hybrid molecules comprising DNA and RNA that may be single-stranded or, more typically, double-stranded, or triple-stranded regions, or a mixture of single- and double-stranded regions. The term "polynucleotide(s)" also embraces short nucleotides or fragments, often referred to as "oligonucleotides", that due to mutagenesis are not 100% identical but nevertheless code for the same amino acid sequence.

By "substantially identical" when referring to a polynucleotide, it will be understood that the polynucleotide of the present description has a nucleic acid sequence which encodes a polypeptide which is at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or any other value between 60 and 99.5% identical to SEQ ID NO: 2, 4 or 6 or functional derivative thereof.

By "substantially identical" when referring to a polynucleotide, it will be understood that the polynucleotide of the present description has a nucleic acid sequence which is at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or any other value between 60 and 99.5% identical to SEQ ID NO: 1, 3 or 5 or functional derivative thereof.

With reference to polynucleotides described herein, the term "isolated polynucleotide" is sometimes used. This term, when applied to DNA, refers to a DNA molecule that is separated from sequences with which it is immediately contiguous to (in the 5' and 3' directions) in the naturally occurring genome of the organism from which it was derived. For example, the "isolated polynucleotide" may comprise a DNA molecule inserted into a vector, such as a plasmid or virus vector, or integrated into the genomic DNA of a prokaryote or eukaryote. An "isolated polynucleotide molecule" may also comprise a cDNA molecule.

As used herein, the term "vector" refers to a polynucleotide construct designed for transduction/transfection of one or more cell types. Vectors may be, for example, cloning vectors which are designed for isolation, propagation and replication of inserted nucleotides, expression vectors which are designed for transcription of a nucleotide sequence in a host cell, or a viral vector which is designed to result in the production of a recombinant virus or virus-like particle, or shuttle vectors, which comprise the attributes of more than one type of vector. A number of vectors suitable for stable transfection of cells and bacteria are available to the public (e.g. plasmids, adenoviruses, baculoviruses, yeast baculoviruses, plant viruses, adeno-associated viruses, retroviruses, Herpes Simplex Viruses, Alphaviruses, Lentiviruses), as are methods for constructing such cell lines. It will be understood that the present application encompasses any type of vector comprising any of the polynucleotide molecules of the present description.

The term "transgenic cell" refers to a genetically engineered cell. Methods for genetically engineering a cell are known such as molecular cloning and gene targeting. These methods can include chemical-based transfection, non-chemical method, particle-based method or viral method. The host cell may be any type of cell such as a transiently-transfected or stably-transfected mammalian cell line, an isolated primary cell, an insect cell, a yeast (*Saccharomyces cerevisiae* or *Pichia pastoris*), a plant cell, a microorganism, or a bacterium (such as *E. coli*).

The expressions "naturally occurring" or "wild-type" refer to material in the form as it occurs in nature. For example, a naturally occurring or wild-type polypeptide or polynucleotide sequence is a sequence present in an organism that is isolated from a source in nature and which has not been intentionally modified by human manipulation. The expressions "Recombinant", "engineered" or "non-naturally occurring": it does not appear in nature, it is an artificial construct, e.g., a cell, nucleic acid, or polypeptide, refers to a material that either has been modified in a manner that would not otherwise be found in nature, or is identical thereto but produced or derived from synthetic materials and/or by manipulation using recombinant techniques.

The expression "reference sequence" refers to a defined sequence to which another sequence is compared. In one implementation, the reference sequence is SEQ ID NO: 2 and preferably SEQ ID NO: 4.

The expression "reference enzyme" is a known enzyme, such as the TACA enzyme or the SspCA enzyme. The activity of the enzyme of the present description is compared to the activity of a reference enzyme.

The expression "coding sequence" refers to the nucleic acid sequence(s) that would yield the amino acid sequence of a given protein/peptide/polypeptide.

The expressions "amino acid", "residue", "amino acid residue" refer to the specific monomer at a sequence position of a polypeptide (e.g., 8C indicates that the "amino acid" or "residue" at position 8 of a given sequence is a cysteine (C). The amino acid may be alanine (3 letter code: ala or one letter code: A), arginine (arg or R), asparagine (asn or N), aspartic acid (asp or D), cysteine (cys or C), glutamine (gin or Q), glutamic acid (glu or E), glycine (gly or G), histidine (his or H), Isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), valine (val or V). Ter indicates a termination/stop codon.

The expression "amino acid difference" refers to an amino acid at a given position in a protein sequence that is different from the one in the reference sequence. It refers to a change in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X8 as compared to SEQ ID NO: 7 refers to a change of the amino acid residue at the polypeptide position corresponding to position 8 of SEQ ID NO: 7. Thus, if the reference polypeptide of SEQ ID NO: 7 has a serine at position 8, then a "residue difference at position X8 as compared to SEQ ID NO: 7" an amino acid substitution of any residue other than glycine at the position of the polypeptide corresponding to position 8 of SEQ ID NO: 7. In most instances herein, the specific amino acid residue difference at a position is indicated as "XnY" where "Xn" specifies the corresponding position as described herein, and "Y" is the single letter identifier of the amino acid found in the engineered polypeptide (i.e., the different residue than in the reference polypeptide). In some instances, the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. For example, "S8C" would refer to the substitution of the amino acid residue, serine (S) at position 8 of reference sequence with the amino acid cysteine (C). In some instances, a polypeptide of the present disclosure can include one or more amino acid residue differences relative to a reference sequence, which is indicated by a list of the specified positions where changes are made relative to the reference sequence. The present disclosure includes engineered polypeptide sequences comprising one or more amino acid differences that include either/or both conservative and non-conservative amino acid substitutions.

The term "non-conservative substitution" refers to an amino acid, at a given position in a protein sequence that is different and not similar from the one in the reference sequence.

The term "deletion" refers to one or several amino acid(s) at a given position in a protein sequence, that is or are absent when compared to the reference sequence.

The term "insertion" refers to one or several amino acid(s) at a given position in a protein sequence, that is or are in excess when compared to the reference sequence.

The term "improved enzyme property" refers to a property that is better in one enzyme when compared to the reference one. It can be an increase in stability toward some denaturing agent, an increase in thermostability, an increase in solvent stability, an increase in pH stability, an increase in enzyme activity, reduced inhibition by products (e.g. bicarbonate and/or carbonate ions), improved stability in presence of the sodium cation, improved stability in presence of the potassium cation, improved solvent solubility, an increase in hydrophilicity, an increase in hydrophobicity or a combination thereof.

The term "stability in presence of" refers to the capacity of the enzyme to remain active over a period of time when in the presence of a denaturing compound. It is usually described as a percentage of remaining activity over time.

The term "thermostability" refers to the capacity of the enzyme to remain active over a period of time when exposed to a given temperature. It is usually described as a percentage of remaining activity over time.

The term "solvent stability" refers to the capacity of the enzyme to remain active over a period of time when exposed to a given solvent (e.g., a $CO_2$ capture solvent such as 1.45 M $KHCO_3/K_2CO_3$ pH 10). It is usually described as a percentage of remaining activity over time.

The term "pH stability" refers to the capacity of the enzyme to remain active over a period of time when exposed to a given pH, such as a higher pH. It is usually described as a percentage of remaining activity over time.

The term "increased enzyme activity" refers to the capacity of an enzyme to catalyze more reaction, such as hydration of $CO_2$ and/or dehydration of the $HCO_3^-$ ion, per time unit than the reference enzyme in some given conditions, such as higher Temperature, higher pH (improved pH activity profile).

The term "increase hydrophilicity" refers to the property of the enzyme to be more soluble in water based absorption solution.

The term "increase hydrophobicity" refers to the property of the enzyme to be less soluble in water based absorption solution.

By "about", it is meant that the relevant value (e.g. of temperature, concentration, pH, etc.) can vary within a certain range depending on the margin of error of the method or apparatus used to evaluate such value. For instance, the margin of error of the temperature may range between $\pm 0.5°$ C. to $\pm 1°$ C., the margin of error of the pH may be $\pm 0.1$ and the margin of error of the concentration may be $\pm 20\%$.

In some implementations, the TACA or functional derivative thereof can be used in a $CO_2$ capture operation where the absorption and desorption stage are run within certain temperature conditions to leverage TACA or functional derivative thereof s temperature and solvent stability. For example, the absorption stage can be operated between 40° C. and 60° C. and the desorption stage can be operated between 40° C. and 85° C. The absorption and desorption stages can also be configured such that the TACA or functional derivative thereof flows through each stage and has residence times within each stage that further leverage the TACA or functional derivative thereof s temperature and solvent stability. For example, the residence time in the absorption stage can be 1 minute to 20 minutes and the residence time in the desorption stage can be 1 minute to 10 minutes. In addition, the concentration of the TACA or functional derivative thereof in the solution can be provided such that catalytic activity is promoted for enhanced residual activity in the $CO_2$ capture process. For example, the TACA or functional derivative thereof can be provided in sufficiently high concentration so as to maintain near 100% residual activity through at least 14 days of operation.

The tests show that the TACA or functional derivative thereof was better than all other tested enzymes between 60 and 98° C. after a certain amount of time. Since TACA or the functional derivative thereof is stable, it may maintain close to 100% residual activity over all temperatures for at least 1 hour. Activity determinations are conducted so there is no over-saturation with enzyme.

As the TACA or functional derivative thereof has been found to have higher residual activity than all of the comparative carbonic anhydrases that were tested, as illustrated in the examples section, the TACA or functional derivative thereof can be used in a $CO_2$ capture operation with greater efficiency and performance compared to other carbonic anhydrases.

In some implementations, the TACA or functional derivative thereof can be used to "top-up" or replenish carbonic anhydride-based $CO_2$ capture operations. The TACA or functional derivative thereof "top-up" or replenishing frequency and amount can be provided such that high catalysis is maintained.

In some implementations, the recombinant TACA or functional derivative thereof can have an improved property relative to the same property of the polypeptide of SEQ ID NO: 4, selected from one or more of improved stability and or activity and or solubility in presence of sodium ion; improved stability and or activity and or solubility in presence of potassium ion; improved stability and or activity and or solubility in presence of carbonate ion; improved stability and or activity and or solubility under high pH conditions; improved stability and or activity and or solubility under high temperature conditions and improved pH-activity profile.

Figure 6:
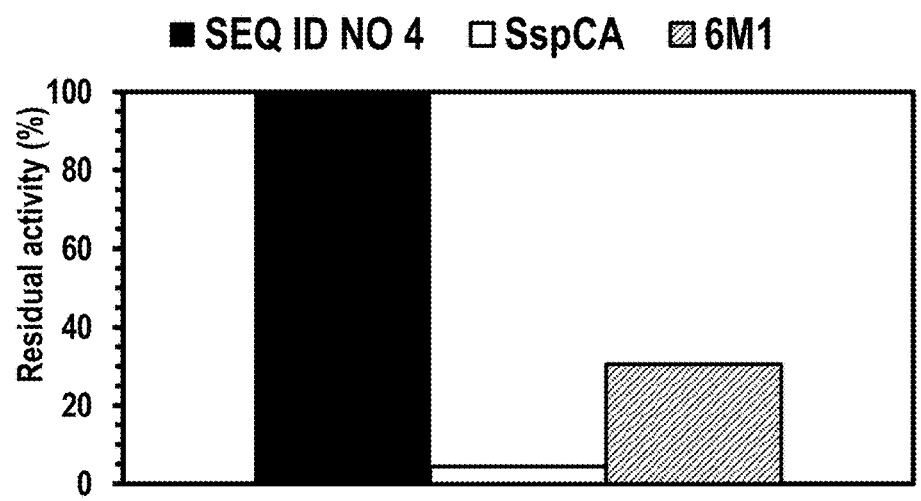
FIG. 6 is a graph of residual activity of various carbonic anhydrases, including TACA (SEQ ID NO: 4), after a 1 hour incubation in 1.45 M $KHCO_3/K_2CO_3$ pH 10 (2.9M $K^+$) at 98° C.
Figure 7:
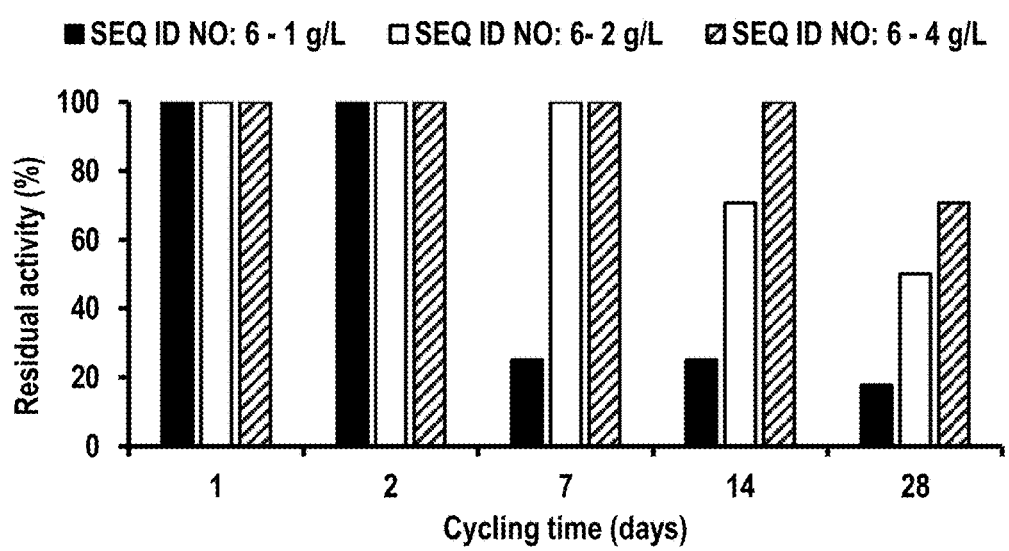
FIG. 7 is a graph of residual activity of TACA (SEQ ID NO: 6 or 7) after different thermal cycling times in 1.45 M $KHCO_3/K_2CO_3$ pH 10 (2.9M $K^+$). Temperature profile for one cycle is given in one cycle lasts 8 minutes and is repeated 180 times per day. A total of 28 days was performed, representing a sum of 5040 cycles. Different enzyme concentrations were tested.

In addition, the TACA or functional derivative thereof assessed in tests reported in the present description display enhanced stability compared to other TACAs assessed by James et al., for example. In James et al., a mild HEPES/NaCl buffer was used and the enzyme was exposed to 90° C. for one hour, resulting in complete deactivation. In contrast, the TACA or functional derivative thereof enzymes of the present disclosure and having structural differences compared to the James et al. enzymes gave enhanced results in terms of enzyme stability. For example, as shown in FIG. 6, TACA retained nearly 100% residual activity when exposed for one hour at 98° C. in 1.45 M $K_2CO_3$ at pH 10.

Various aspects of the present description will be more readily understood by referring to the following examples. These examples are illustrative of the wide range of applicability of the present description and are not intended to limit its scope. Modifications and variations can be made therein without departing from the spirit and scope of the description. Although any methods and materials similar or equivalent to those described herein can be used in the practice for testing of the present description, the preferred methods and materials are described.

The scope of the claims should not be limited by the aspects, scenarios, implementations, examples or embodiments set forth in the examples and the description, but should be given the broadest interpretation consistent with the description as a whole.

The issued patents, published patent applications, and references that are mentioned herein are hereby incorporated by reference. In the case of inconsistencies, the present disclosure will prevail.

EXAMPLES

Example 1: Materials, Methods and Producing of TACA Enzymes

TACA enzymes were constructed, expressed, and purified as follows. Using standard recombinant methods, the first 20 amino acids of the wild-type TACA enzyme (see FIG. 1; SEQ ID NO: 2), corresponding to its N-terminal signal sequence, were removed and replaced with a single methionine residue, giving a truncated TACA enzyme having the amino acid sequence of SEQ ID NO: 4. It was subsequently found that higher expression levels of the truncated TACA enzyme in a bacterial expression host could be obtained by further replacing the first six amino acid residues ("MGGGAH") of the enzyme of SEQ ID NO: 4 with the residues "MEHE", giving the TACA enzyme set forth in SEQ ID NOs: 6 and 7. For greater clarity, SEQ ID NOs: 6 and 7 refer to the same protein and may be used interchangeably.

Following codon-optimization of the TACA coding sequences, they were cloned into expression vectors which employed either a T5 or T7 promoter and expressed in an *E. coli* BL21-derived strain. TACA enzymes were purified by heat purification and other standard techniques.

Following its purification, the TACA enzyme having the amino acid sequence of SEQ ID NO: 4 (hereafter referred to as "wtTACA") was characterized in a $CO_2$ capture column and by a pH indicator-based technique. The $CO_2$ capture column consists in contacting a gas containing 14% v/v $CO_2$ and a $CO_2$-capture solvent consisting of 1.45 M $KHCO_3$/$K_2CO_3$ pH 10 at 25° C. When present, the enzyme is dissolved in the solvent at a concentration of 0.2 g/L. The solvent flows inside a 50 cm height packed column from top to the bottom. The $CO_2$-containing gas flows counter currently inside the same column. The liquid to gas flowrate ratio is adjusted to 50 g/g. A gas analyzer measures the $CO_2$ concentration in the gas at the inlet and outlet of the column. In these conditions, a 90% $CO_2$ removal efficiency was obtained confirming the high activity level of TACA.

The pH indicator-based technique was performed to compare the stability and activity of TACA with those of other carbonic anhydrases. More specifically, the TACA of SEQ ID NO: 4 was compared with the following other carbonic anhydrases:

(i) Carbonic anhydrase from *Sulfurihydrogenibium* sp. referred as "SspCA" (SEQ ID NO: 8) and described in patent application WO2014066999 A1, which shares 49% amino acid sequence identity with SEQ ID NO: 4 by performing a protein BLAST; and (ii) A thermostable variant of SspCA referred to as "6M1" (SEQ ID NO: 9), described in patent application WO2014066999 A1 (see SEQ ID NO: 196 therein), which shares 50% amino acid sequence identity with SEQ ID NO: 4 by performing a protein BLAST.

Using the pH-indicator-based technique, the three tested carbonic anhydrases (i.e., TACA, SspCA, and 6M1; SEQ ID NOs: 4, 8, and 9, respectively) returned about the same activity level. To assess their respective stabilities, their residual activity was evaluated after 1 h exposure at 98° C. in 1.45 M $K_2CO_3$, pH 10. While the TACA of SEQ ID NO: 4 retained nearly 100% residual activity, SspCA and 6M1 retain only about 5% and 30% residual activities, respectively.

Example 2: Performance of TACA in a Packed Column Absorption Unit

An experiment was conducted in an absorption packed column. The absorption solution is an aqueous solution of potassium carbonate 1.45 M at pH 10. This absorption solution is contacted counter-currently with a gas phase with a $CO_2$ concentration of 130,000 ppm. Liquid flow rate was 500 g/min and gas flow rate was 10 g/min corresponding to L/G of 50 g/g. Gas and absorption solution were at room temperature. The column has a 7.5 cm diameter and a 50 cm height. Packing material is polymeric Raschig™ rings 6 mm. The TACA concentration was 0.2 g/L. The results showed that $CO_2$ transfer rate of $CO_2$ removal rate increased from 4.7 mmol/sec for the solution to 40 mmol/sec when adding the enzyme to the absorption solution. TACA (SEQ ID NO: 4) increased the $CO_2$ removal rate by 8.5 fold under these conditions.

Example 3: Stability of TACA Compared to that of SspCA and 6M1

The stability of TACA, SspCA and 6M1 (SEQ ID NOs: 4 & 6, 8, and 9, respectively) enzymes was compared. The stability was evaluated by exposing the enzymes to an absorption solution including 1.45 M $KHCO_3/K_2CO_3$ (2.9 M $K^+$) pH 10 and 20% w/v MDEA alpha=0.1 at various temperatures for different exposure times. As shown in FIGS. 2 to 9, TACA (both SEQ ID NOs: 4 and 6) exhibited the highest stability in all the tested conditions, as compared to the SspCA and 6M1 enzymes.

Figure 3:
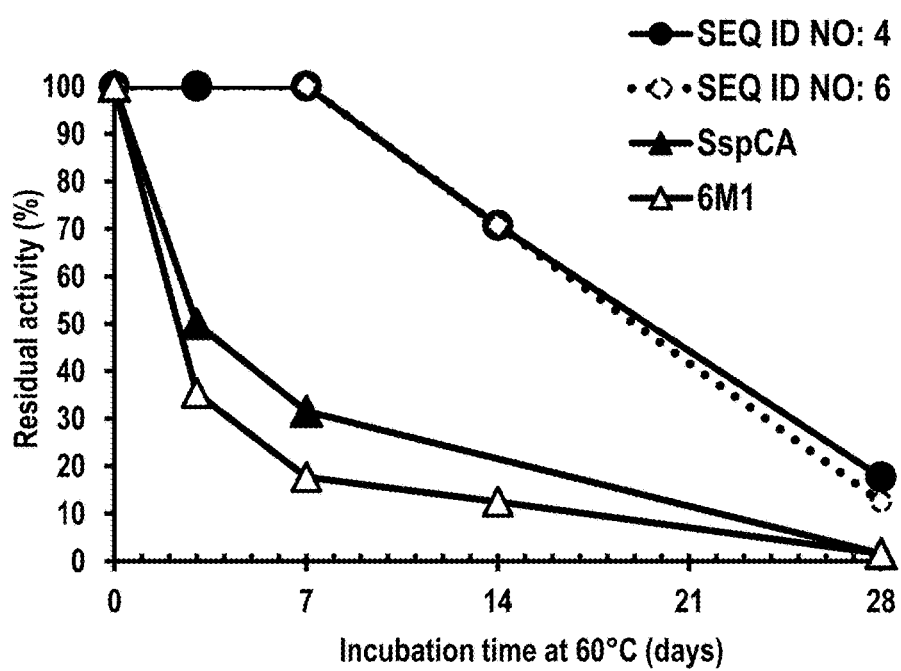
FIG. 3 is a graph of residual activity of various carbonic anhydrases, including TACA (SEQ ID NO: 4 and 6), after various incubation times in 1.45 M $KHCO_3/K_2CO_3$ pH 10 (2.9M $K^+$) at 60° C.
Figure 4:
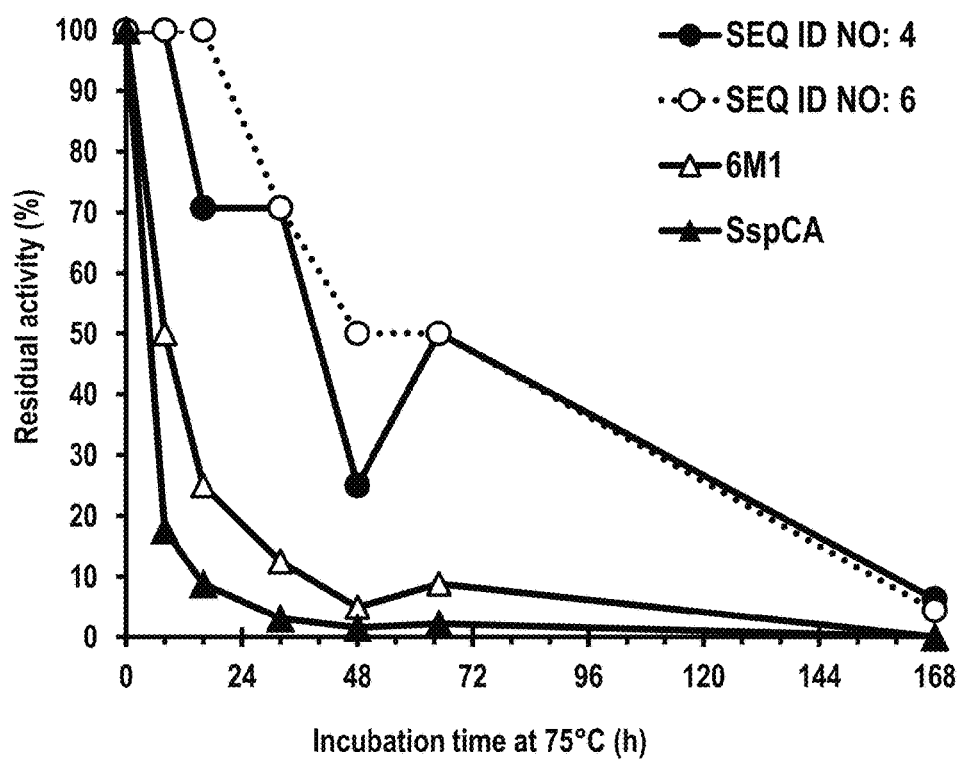
FIG. 4 is a graph of residual activity of various carbonic anhydrases, including TACA (SEQ ID NO: 4 and 6), after various incubation times in 1.45 M $KHCO_3/K_2CO_3$ pH 10 (2.9M $K^+$) at 75° C.
Figure 5:
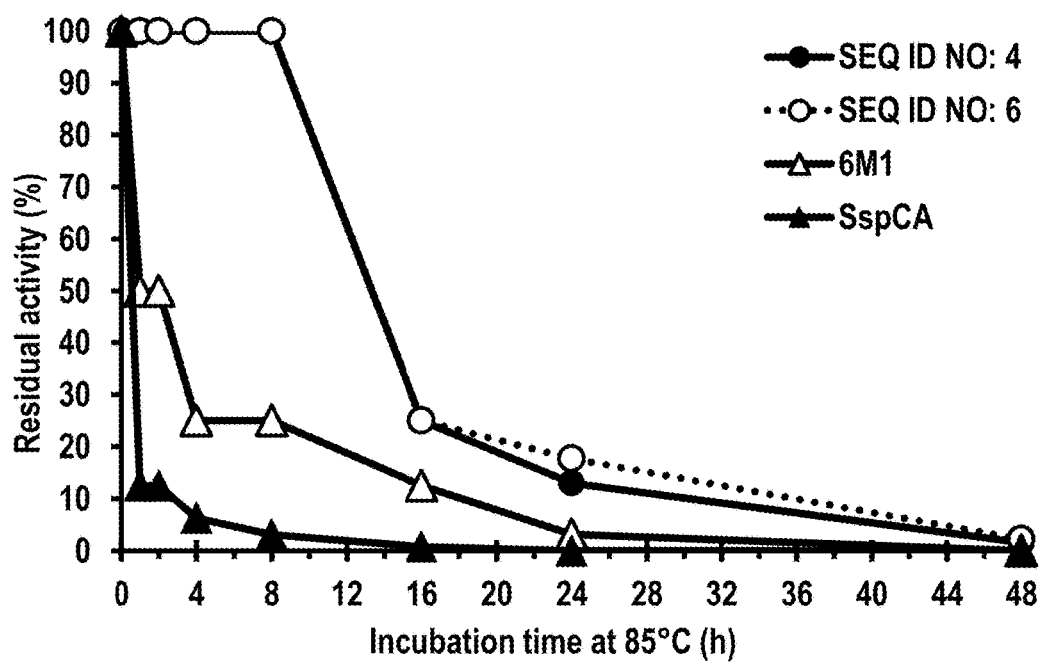
FIG. 5 is a graph of residual activity of various carbonic anhydrases, including TACA (SEQ ID NO: 4 and 6), after various incubation times in 1.45 M $KHCO_3/K_2CO_3$ pH 10 (2.9M $K^+$) at 85° C.

As shown in FIG. 3, in 1.45 M $KHCO_3/K_2CO_3$ (2.9M $K^+$) pH 10, TACA retained all of its activity after one week incubation at 60° C., while the SspCA and 6M1 enzymes lost more than 60% of their initial activity. Furthermore, TACA showed 50% residual activity after 60 hours incubation at 75° C., while other enzyme returned 10% or less residual activity levels (FIG. 4). TACA also retained the most activity at higher temperatures, such as at 85° C. (FIG. 5) and at 98° C. (FIG. 6).

Figure 8:
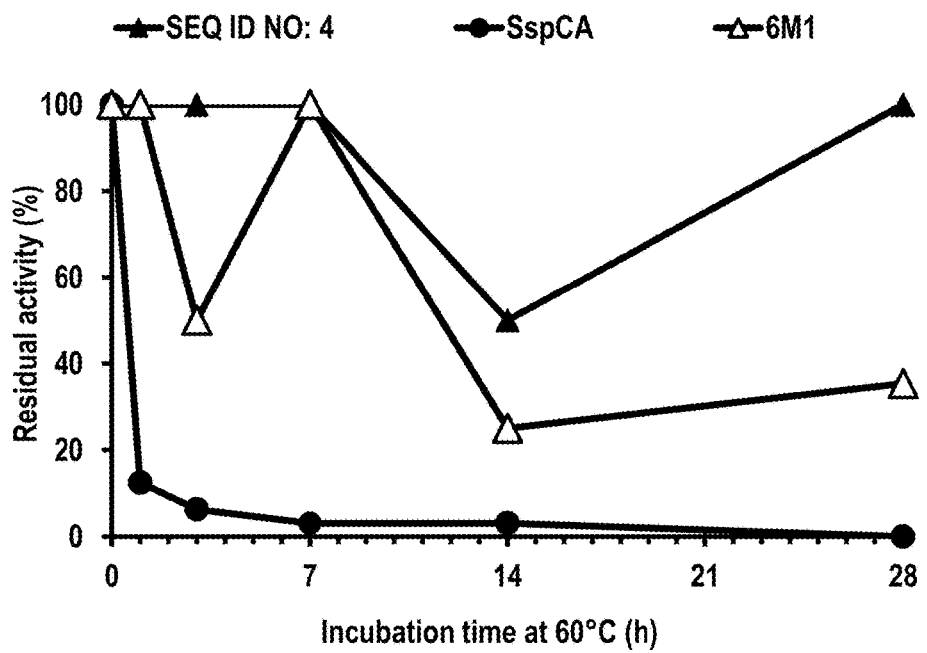
FIG. 8 is a graph of residual activity of various carbonic anhydrases, including TACA (SEQ ID NO: 4), after various incubation times in 20% MDEA alpha=0.1 (mol $CO_2$/mol MDEA) at 60° C.

As shown in FIG. 8, TACA retained 100% of its initial activity after 28 days incubation at 60° C. in 20% MDEA alpha=0.1. During the same time, SspCA was completely inactivated while 6M1 still exhibited some activity.

Example 4: Stability of TACA Compared to that SspCA and 6M1 in the Context of Thermal Cycling in 1.45 M $KHCO_3/K_2CO_3$ (2.9M $K^+$) pH 10

Figure 9:
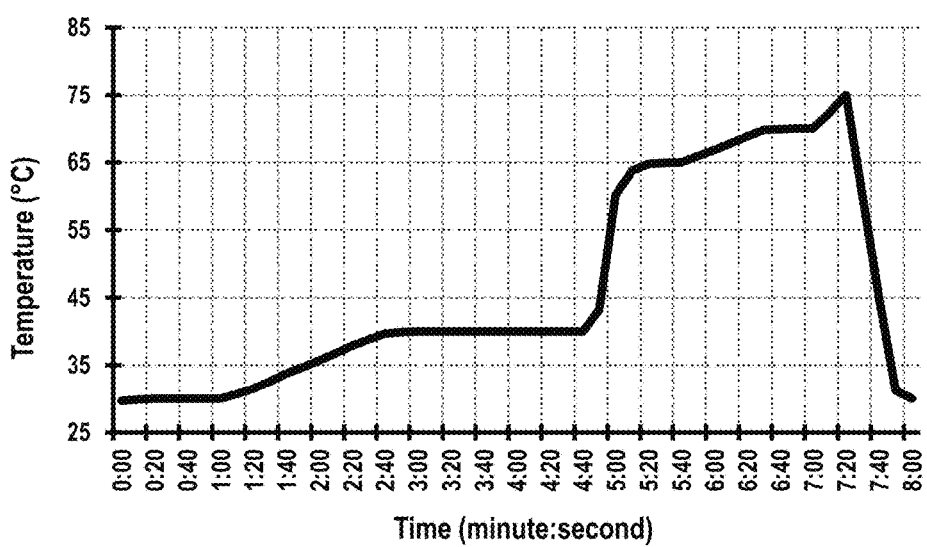
FIG. 9 is related to thermal cycling described in FIG. 8 and shows temperature fluctuations occurring in one cycle representative of a $CO_2$ capture process.

In industrial application, enzymes will have to deal with temperature fluctuations. To test the enzyme stability in this context, a thermal cycling test was conducted on TACA. The enzyme was subjected to temperature fluctuations occurring between 30° C. and 75° C. FIG. 9 shows temperature profile occurring for each cycle which lasts about 8 minutes. This cycle was repeated 180 times per day for 28 days, giving a total of 5040 cycles. Under these conditions, TACA retained about 50-100% residual activity level after 7-14 days. About 25-50% activity level was recorded after 28 days.

Example 5: Comparison of Amino Acid Sequences Between Carbonic Anhydrase Obtained from *Thermovibrio ammonificans* and the Most Similar Protein in GenBank The Table below shows sequence similarities between TACA and the most similar proteins in GenBank, including a carbonic anhydrase from *Persephonella marina* SspCA and the variant 6M1 from said SspCA, which were identified by performing a protein BLAST against known sequences in GenBank.

As shown in the Table below, the most similar carbonic anhydrases to the TACA carbonic anhydrase obtained from *Thermovibrio ammonificans* was found in *P. marina* with 66% identity. SspCA, not shown in the Table below, was ranked as the 375th most similar protein.

| Genbank accession number | Description | Query cover | Identity |
|---|---|---|---|
| WP_013538320.1 | carbonic anhydrase [*Thermovibrio ammonificans*] | 98% | 100% |
| WP_015898908.1 | carbonic anhydrase [*Persephonella marina*] | 98% | 66% |
| WP_029522463.1 | carbonic anhydrase [*Persephonella* sp. KM09-Lau-8] | 98% | 63% |
| WP_029521561.1 | carbonic anhydrase [*Persephonella* sp. IF05-L8] | 98% | 61% |
| WP_007474387.1 | carbonic anhydrase [*Caminibacter mediatlanticus*] | 98% | 59% |
| WP_028579713.1 | hypothetical protein [*Desulfobulbus japonicus*] | 98% | 52% |
| WP_019445033.1 | carbonic anhydrase [*Aeromonas* sp. 159] | 98% | 53% |
| WP_007040788.1 | carbonic anhydrase [*Thiorhodococcus drewsii*] | 98% | 52% |
| WP_005354260.1 | carbonic anhydrase [*Aeromonas veronii*] | 98% | 53% |
| WP_005362587.1 | carbonic anhydrase [*Aeromonas veronii*] | 98% | 53% |
| WP_005348316.1 | carbonic anhydrase [*Aeromonas veronii*] | 98% | 53% |
| WP_007766615.1 | carbonic anhydrase [*Cronobacter turicensis*] | 100% | 49% |
| WP_012459296.1 | carbonic anhydrase [*Sulfurihydrogenibium* sp. YO3AOP1 (SspCA)] | 97% | 49% |
| not applicable | SspCA variant "6M1" (SEQ ID NO: 9) | 97% | 50% |

Example 6: TACA's Stability Improvement in Carbonate-Based Buffer

Recombinant (or engineered) carbonic anhydrase (CA) polypeptides having improved properties relative to wild-type TACA (SEQ ID NO: 4) were generated. The latter CAs are hereafter referred to as improved variants. The improved variants were generated using directed evolution techniques that are well known by those skilled in the art.

The improved properties included one or more of: improved thermostability, improved activity (hydration of $CO_2$ and/or dehydration of the $HCO_3^-$ ion), improved high pH stability (e.g. pH 7 to 12), improved pH activity profile, reduced inhibition by products (e.g., bicarbonate and/or carbonate ions), improved stability in presence of the sodium cation, improved stability in presence of the potassium cation, improved solvent solubility, reduced inhibition by gas contaminants, or any combination thereof.

The improved variants comprise at least one or more amino acid substitutions in their amino acid sequence relative to that of wild-type TACA (SEQ ID NO: 4) or the truncated TACA N-terminal derivative of SEQ ID NO: 6 or 7, that results in CA exhibiting improved properties. An improved variant can have in its amino acid sequence 1 or more substitutions, 2 or more substitutions, 3 or more substitutions, 4 or more substitutions, 5 or more substitutions, 6 or more substitutions, 7 or more substitutions, 8 or more substitutions, 9 or more substitutions, 10 or more substitutions. The improved variant may additionally comprise neutral mutations. The improved variant can be substantially identical to TACA. By "substantially identical", it is meant that the sequence of the present description has an amino acid sequence which is at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% identical to SEQ ID NO: 4, 6, 7 or 10. The mutations comprise but are not limited to any mutations at positions listed in Table 3, or any functional derivative thereof. The mutation can be conservative or non-conservative. Non-limiting examples of conservative mutations are given in Table 1. Conservative mutations are known to usually provide similar effect to protein structure and function. The functional derivative can comprise substitution(s), insertion(s) and/or deletion(s), or combination thereof. The variant can be free or immobilized.

TABLE 1

Possible conservative mutations

| Class | Amino acid | Conservative mutation class |
|---|---|---|
| Non-polar | A, V, L, I | Non-polar |
| | | Other non-polar |
| Other non-polar | G, M | Non-polar |
| Aromatic | H, F, Y, W | Aromatic |
| Polar | Q, N, S, T | Polar > acidic, basic |
| Acidic | D, E | Acidic > polar |
| Basic | K, R | Basic > polar |
| Other | C, P | None |

The functional derivative can have any substitution at surface-exposed residues. It is known by those skilled in the art that most neutral substitutions, i.e. mutations that retain biological and biophysical properties of a given protein, are found at these positions. Mutations tend also to be found at residues not involved in the function of the protein and away from the active site region. Table 2 describes the location and features of every TACA residue in its 3D-structure (PDB ID 4C3T).

TABLE 2

Location and features of TACA residues based on their 3D-structure

| Position | Solvent exposure | Other feature |
|---|---|---|
| X1 | Exposed | |
| X2 | Exposed | |
| X3 | Exposed | |
| X4 | Exposed | |
| X5 | Exposed | |
| X6 | Partially exposed | |
| X7 | Exposed | |
| X8 | Exposed | |
| X9 | Exposed | |
| X10 | Exposed | |
| X11 | Exposed | |
| X12 | Partially exposed | |
| X13 | Exposed | |
| X14 | Exposed | |
| X15 | Exposed | |
| X16 | Buried | |
| X17 | Partially exposed | |
| X18 | Exposed | |
| X19 | Exposed | |
| X20 | Exposed | |
| X21 | Exposed | |
| X22 | Exposed | |
| X23 | Exposed | |
| X24 | Exposed | Dimer interface |
| X25 | Exposed | Dimer interface |
| X26 | Partially exposed | Intramolecular disulfide bridge |
| X27 | Exposed | |
| X28 | Exposed | Dimer interface |
| X29 | Exposed | |
| X30 | Exposed | Dimer interface |
| X31 | Buried | Dimer interface |
| X32 | Exposed | |
| X33 | Buried | |
| X34 | Buried | |
| X35 | Partially exposed | |
| X36 | Exposed | |
| X37 | Partially exposed | |
| X38 | Exposed | |
| X39 | Exposed | |
| X40 | Exposed | |
| X41 | Exposed | |
| X42 | Exposed | |
| X43 | Exposed | Dimer interface |
| X44 | Exposed | |
| X45 | Partially exposed | Dimer & tetramer interface |
| X46 | Exposed | Intermolecular disulfide bridge, Tetramer interface |
| X47 | Partially exposed | |
| X48 | Exposed | |
| X49 | Exposed | |
| X50 | Partially exposed | |
| X51 | Exposed | |
| X52 | Exposed | |
| X53 | Exposed | |
| X54 | Exposed | |
| X55 | Exposed | |
| X56 | Exposed | |
| X57 | Exposed | |
| X58 | Exposed | |
| X59 | Exposed | |
| X60 | Exposed | |
| X61 | Buried | |
| X62 | Exposed | |
| X63 | Partially exposed | |
| X64 | Exposed | |
| X65 | Exposed | |
| X66 | Exposed | Proton shuttle |
| X67 | Exposed | |
| X68 | Buried | |
| X69 | Exposed | |
| X70 | Buried | |
| X71 | Exposed | |
| X72 | Partially exposed | |
| X73 | Exposed | |
| X74 | Exposed | |
| X75 | Exposed | |
| X76 | Partially exposed | |
| X77 | Exposed | |
| X78 | Buried | |
| X79 | Exposed | |
| X80 | Partially exposed | |
| X81 | Exposed | Dimer interface |
| X82 | Exposed | |
| X83 | Exposed | |
| X84 | Exposed | |
| X85 | Buried | |
| X86 | Exposed | |
| X87 | Buried | |
| X88 | Exposed | |
| X89 | Exposed | |
| X90 | Buried | |
| X91 | Buried | Metal coordinating |
| X92 | Buried | |
| X93 | Buried | Metal coordinating |
| X94 | Partially exposed | |
| X95 | Exposed | |
| X96 | Buried | |
| X97 | Buried | |
| X98 | Buried | |
| X99 | Exposed | |
| X100 | Exposed | |

TABLE 2-continued

Location and features of TACA residues based on their 3D-structure

| Position | Solvent exposure | Other feature |
|---|---|---|
| X101 | Exposed | |
| X102 | Exposed | |
| X103 | Exposed | |
| X104 | Exposed | |
| X105 | Exposed | |
| X106 | Exposed | |
| X107 | Buried | |
| X108 | Buried | |
| X109 | Buried | |
| X110 | Buried | Metal coordinating |
| X111 | Buried | |
| X112 | Exposed | Active site pocket |
| X113 | Buried | |
| X114 | Exposed | |
| X115 | Exposed | |
| X116 | Exposed | |
| X117 | Exposed | |
| X118 | Exposed | |
| X119 | Exposed | |
| X120 | Exposed | |
| X121 | Buried | |
| X122 | Partially exposed | Active site pocket |
| X123 | Buried | |
| X124 | Buried | |
| X125 | Buried | |
| X126 | Buried | |
| X127 | Buried | |
| X128 | Exposed | |
| X129 | Exposed | |
| X130 | Exposed | |
| X131 | Exposed | |
| X132 | Exposed | |
| X133 | Exposed | |
| X134 | Exposed | |
| X135 | Exposed | |
| X136 | Buried | |
| X137 | Exposed | |
| X138 | Exposed | |
| X139 | Buried | |
| X140 | Partially exposed | |
| X141 | Exposed | |
| X142 | Exposed | |
| X143 | Exposed | |
| X144 | Exposed | |
| X145 | Exposed | |
| X146 | Exposed | |
| X147 | Exposed | |
| X148 | Exposed | |
| X149 | Exposed | |
| X150 | Exposed | |
| X151 | Exposed | |
| X152 | Exposed | |
| X153 | Partially exposed | |
| X154 | Exposed | |
| X155 | Exposed | |
| X156 | Exposed | |
| X157 | Buried | |
| X158 | Exposed | |
| X159 | Exposed | |
| X160 | Exposed | |
| X161 | Exposed | |
| X162 | Buried | |
| X163 | Partially exposed | |
| X164 | Partially exposed | |
| X165 | Exposed | |
| X166 | Exposed | |
| X167 | Exposed | |
| X168 | Exposed | |
| X169 | Exposed | |
| X170 | Exposed | |
| X171 | Buried | Dimer interface |
| X172 | Buried | |
| X173 | Buried | Dimer interface |
| X174 | Buried | |
| X175 | Buried | |
| X176 | Exposed | Active site pocket |
| X177 | Exposed | Active site pocket |
| X178 | Exposed | Active site pocket |
| X179 | Exposed | Active site pocket |
| X180 | Exposed | Active site pocket |
| X181 | Buried | Intermolecular disulfide bridge |
| X182 | Exposed | |
| X183 | Exposed | Dimer interface |
| X184 | Exposed | Dimer interface |
| X185 | Partially exposed | |
| X186 | Partially exposed | Dimer interface |
| X187 | Buried | |
| X188 | Buried | |
| X189 | Buried | |
| X190 | Buried | |
| X191 | Exposed | |
| X192 | Exposed | |
| X193 | Exposed | |
| X194 | Exposed | |
| X195 | Exposed | |
| X196 | Buried | |
| X197 | Exposed | |
| X198 | Exposed | |
| X199 | Exposed | |
| X200 | Partially exposed | |
| X201 | Partially exposed | |
| X202 | Exposed | |
| X203 | Exposed | |
| X204 | Buried | |
| X205 | Exposed | |
| X206 | Exposed | |
| X207 | Exposed | |
| X208 | Exposed | |
| X209 | Exposed | |
| X210 | Exposed | |
| X211 | Exposed | |
| X212 | Buried | |
| X213 | Exposed | |
| X214 | Partially exposed | |
| X215 | Exposed | |
| X216 | Exposed | |
| X217 | Exposed | |
| X218 | Exposed | |
| X219 | Exposed | Dimer interface |
| X220 | Exposed | Dimer interface |
| X221 | Buried | Dimer interface |
| X222 | Buried | Dimer interface |
| X223 | Partially exposed | Dimer interface |
| X224 | Buried | |
| X225 | Buried | Dimer interface |
| X226 | Partially exposed | Tetramer interface |

A number of TACA variants displaying improved stability, as compared to the TACA enzyme of SEQ ID NO: 7, were identified using directed evolution techniques. These directed evolution techniques involved exposing the variants to conditions suitable for $CO_2$-capture (1.45 M $K_2CO_3$ pH 10 at temperatures ≥70° C.), and measuring their activity. Variants that were made and tested include those shown in Table 3.

TABLE 3

TACA variants tested for enhanced stability in 1.45M $K_2CO_3$ pH 10 at a temperature ≥ 70° C.

| Amino acid substitution (residue numbering according to SEQ ID NO: 7) | | Temperature | | |
|---|---|---|---|---|
| 3-letter code | 1-letter code | 90° C. | 85° C. | 70° C. |
| Glu2Gln | E2Q | ★ | – | – |
| Glu2Val | E2V | ★★ | – | – |
| Trp5Cys | W5C | ★★★ | ★★★ | ★★★★ |
| Trp5Arg | W5R | ★★★ | ★★★ | NA |
| Tyr7Cys | Y7C | ★★★ | ★ | NA |
| Tyr7His | Y7H | ★★★ | ★★ | NA |
| Tyr7Phe | Y7F | ★★★ | ★★ | NA |
| Ser8Cys | S8C | ★★★ | ★★ | ★★★★★ |
| Gly9Cys | G9C | ★★ | ★★ | – |
| Gly9Pro | G9P | ★★ | ★★ | – |
| Gly9Asn | G9N | NA | NA | NA |
| Gly12Asp | G12D | ★ | ★ | – |
| Gly12Arg | G12R | ★★ | ★★ | ★ |
| Gly12Val | G12V | ★★ | ★ | ★ |
| Pro13Gln | P13Q | ★★ | ★ | – |
| Trp16Arg | W16R | ★★ | ★★ | NA |
| Trp16Cys | W16C | ★★ | – | NA |
| Trp16Gly | W16G | ★★ | ★ | NA |
| Gly17Cys | G17C | ★★★ | ★★★ | NA |
| Asp18Val | D18V | ★★★ | ★★ | NA |
| Pro21Leu | P21L | ★ | ★ | ★★ |
| Pro21Lys | P21K | – | – | – |
| Glu22Lys | E22K | – | ★ | – |
| Glu22Pro | E22P | ★★★★ | ★★★★ | ★ |
| Glu22Leu | E22L | ★★ | ★★★ | – |
| Asn31Cys | N31C | – | – | – |
| Ser51Ile | S51I | – | – | – |
| Val52Ile | V52I | – | ★ | ★★★ |
| Gly73Cys | G73C | ★ | ★ | ★★ |
| Gly76Asp | G76D | – | – | – |
| Tyr77Asp | Y77D | ★★ | ★ | – |
| Gly82Ser | G82S | – | – | – |
| Asn101Gln | N101Q | – | – | – |
| Lys103Met | K103M | – | – | NA |
| Asp115Asn | D115N | – | – | – |
| Lys116Asn | K116N | – | – | ★ |
| Asn117Gln | N117Q | – | – | – |
| Val125Ala | V125A | ★★ | ★ | – |
| Phe126Leu | F126L | – | – | ★ |
| Lys131Ile | K131I | ★★ | ★★ | – |
| Lys138Asn | K138N | ★ | – | – |
| Arg141His | R141H | – | – | – |
| Arg151Cys | R151C | – | – | – |
| Ser173Cys | S173C | – | – | – |
| Cys181Tyr | C181Y | – | – | – |
| Phe190Cys | F190C | – | – | ★★ |
| Gly12Asp, Pro21Gln | G12D, P21Q | NA | NA | NA |
| Gly12Asp, K27Thr | G12D, K27T | NA | NA | NA |
| Gly12Asp, Val142Ile | G12D, V142I | NA | NA | NA |
| Trp16Cys, Arg167Ser | W16C, R167S | NA | NA | NA |
| Trp16Arg, Lys206Thr | W16R, K206T | NA | NA | NA |
| Trp16Gly, Val50Met | W16G, V50M | NA | NA | NA |
| Leu19Ser, Lys138Arg | L19S, K138R | NA | NA | NA |
| Leu19Ser, Asp158Gly | L19S, D158G | NA | NA | NA |
| Lys150Met, Pro193Ser | K150M, P193S | – | ★ | – |
| Phe190Met, Pro193Ser | F190M, P193S | ★ | ★ | NA |
| Arg141His, Arg151Cys | R141H, R151C | – | ★ | – |
| Ser8Cys, Arg141His | S8C, R141H | ★★ | ★ | – |
| Ser8Cys, Arg151Cys | S8C, R151C | ★★★ | ★★ | – |
| Ser8Cys, Arg141His, Arg151Cys | S8C, R141H, R151C | ★ | – | ★★ |
| Gly9Pro, Pro21Asp | G9P, P21D | NA | NA | NA |
| Gly9Pro, Pro21Asn | G9P, P21N | NA | NA | NA |
| Gly9Pro, Pro21Gln | G9P, P21Q | NA | NA | NA |
| Gly9Pro, Pro21Val | G9P, P21V | NA | NA | NA |
| Gly9Pro, Pro21Gly | G9P, P21G | NA | NA | NA |
| Gly9Pro, Glu22Pro | G9P, E22P | ★★★★ | ★★★★ | – |
| Ser8Arg, Gly9Pro, Glu22Pro | S8R/G9P/E22P | ★★★★★ | ★★★★★ | ★★★★ |
| Ter227Tyr, Gly228, Ter* | Ter227Y, G228, Ter* | ★ | ★★ | ★★★ |
| Ser8Arg | S8R | ★ | ★ | NA |
| Arg156Glu | R156E | ★★ | ★★ | ★★★ |

TABLE 3-continued

TACA variants tested for enhanced stability in 1.45M $K_2CO_3$
pH 10 at a temperature ≥ 70° C.

| Amino acid substitution (residue numbering according to SEQ ID NO: 7) | | Temperature | | |
|---|---|---|---|---|
| 3-letter code | 1-letter code | 90° C. | 85° C. | 70° C. |
| Ser8Arg, Gly9Pro, Glu22Pro, Arg156Glu | S8R/G9P/E22P/R156E | ★★★★ | ★★★★ | ★★★ |

*"Ter" is the abbreviation for the Stop codon. The stop codon in SEQ ID NO: 7 was replaced with the insertion of Tyr-Gly in the variant "Ter227Y, G228, Ter"
− Half-life about that of SEQ ID NO: 7 or less
★ Half-life between 100% to 125% that of SEQ ID NO: 7
★★ Half-life between 125% to 150% that of SEQ ID NO: 7
★★★ Half-life between 150% to 200% that of SEQ ID NO: 7
★★★★ Half-life between 200% to 300% that of SEQ ID NO: 7
★★★★★ Half-life over 300% that of SEQ ID NO: 7

Strikingly, the above data clearly show that most of the beneficial mutations in the enzymatic conditions tested are found in the first 22 residues of TACA. Moreover, multiple mutations were identified at nine amino acid positions (i.e., X2, X5, X7, X8, X9, X12, X16, X21, and X22). Taken together, these results suggest that this region of the wild-type TACA enzyme is not optimal for $CO_2$ capture, and may be engineered to obtain an enzyme having improved properties in a $CO_2$ capture solvent. These results also show that there are multiple routes possible, for someone skilled in the art of protein engineering, to improve this particular region.

Example 6b: Stability of the TACA S8R/G9P/E22P Variant in Different $CO_2$ Capture Solvents The impact of mutations in various $CO_2$ capture solvent was assessed. To do so, stability of TACA (SEQ ID NO: 7) was compared to that of a TACA variant containing three mutations (i.e., S8R/G9P/E22P). Both enzymes were incubated at 85° C. in these $CO_2$ capture solvents:
1.45 M $K_2CO_3$ pH 10.0
0.3 M $Na_2CO_3$ pH 10.0
2 M MDEA
2.4 M potassium N,N-dimethylglycine (pH 10.3)
For all tested solvents, a 2 g/L enzyme concentration was used. Residual activity level was determined over time.

Figure 14:
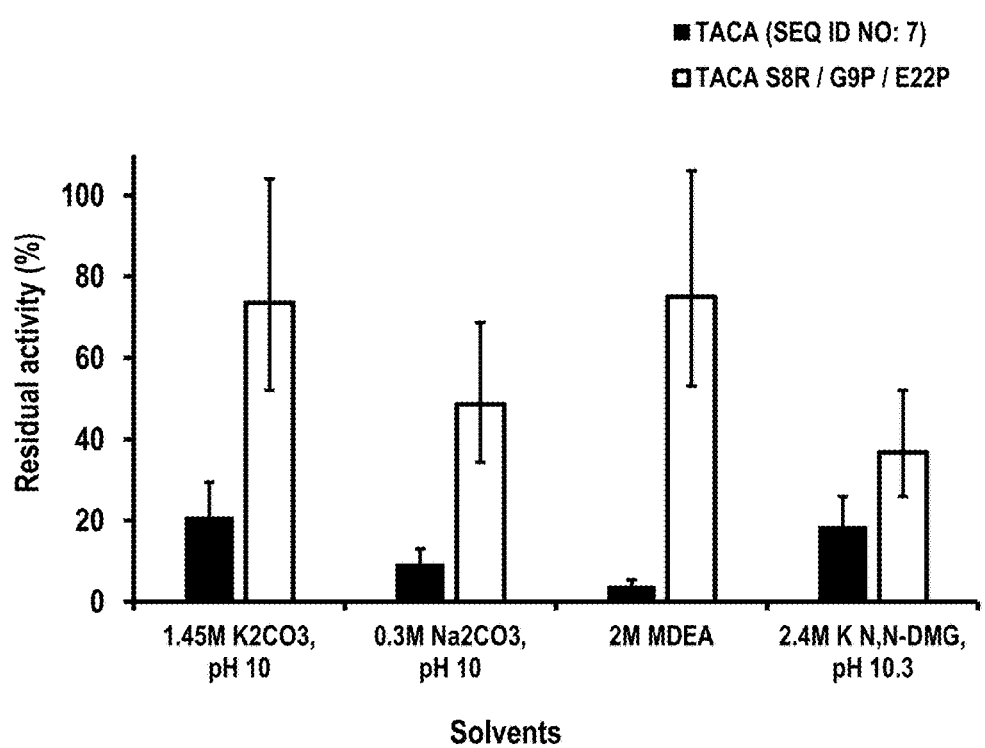
FIG. 14 is a graph showing residual activity level of TACA (SEQ ID NO: 6 or 7) and one TACA variant containing three mutations (SBR/G9P/E22P) after 1 day incubation at 85° C. in various $CO_2$ capture solvents.

As shown in FIG. 14, the TACA S8R/G9P/E22P variant showed increased stability in comparison to the TACA of SEQ ID NO: 7 in all of the tested solvents. These results confirm that, despite the fact that these mutants were initially selected for their higher stability in 1.45 M $K_2CO_3$, they can confer a beneficial impact in other solvents. That being said, the extent of the stability improvement provided by the variants, may vary from one solvent to another. For this particular TACA S8R/G9P/E22P variant, the stability increase was greater in for example 2 M MDEA than in 2.4 M potassium N,N-dimethylglycine.

Example 7: Stability of the TACA Under Temperature Cycling Conditions

To confirm the potential of TACA (or functional derivatives thereof) for use in $CO_2$ capture operations, its stability was evaluated under temperature cycling conditions to mimic the process conditions to which it would be exposed. 1.2 L of a 1.45 M $K_2CO_3$ solution at a $CO_2$ loading of 0.63 (pH 10), containing 2 g/L of TACA enzyme (SEQ ID NO: 6), exposed to a 40° C. was continuously pumped through a water bath at a temperature of 77° C. where its temperature was increased for 4 minutes. Then the solution was pumped back to the reservoir at 40° C. A temperature of 40° C. is typical of conditions in an absorption unit and higher temperatures are representative of temperature to be encountered in a desorption unit. The solution was exposed to these temperature cycling conditions on 24h per day and 7d per week basis. At specific exposure times, samples of the solution were withdrawn for activity measurement. $CO_2$ hydration activity of TACA or functional derivative thereof was measured at 25° C. in a 1.45 M $K_2CO_3$ pH 10 solution, TACA or derivative thereof concentration for the assay was 0.2 g/L.

Residual activity data for TACA or derivative thereof are shown in FIG. 15. The results show that this enzyme keeps at least 80% of its initial activity for at least 20 days. In the context of an industrial use of this enzyme in a $CO_2$ capture unit, this clearly demonstrates that the enzyme is robust towards industrially relevant operation conditions characterized by salt concentration higher than 0.5 M and alkaline pH.

These tests show that TACA or a functional derivative thereof has remarkable stability even in practical process conditions, which are relatively harsh when compared to standard laboratory conditions.

Example 8: Cyclic Process Performance

The industrial relevance of TACA (SEQ ID NO: 6 or 7) was demonstrated in a 1 ton per day $CO_2$ capture pilot unit located at the University of North Dakota's Energy & Environmental Research Center (EERC). The $CO_2$ capture unit included a packed column absorber and a packed column stripper/desorber. The TACA enzyme was used in combination with a 1.45 M $K_2CO_3$ solution to capture $CO_2$ from a gas effluent. Two types of gas effluents were tested: one from natural gas combustion and a second from coal combustion. $CO_2$ concentration in the flue gas from the natural gas combustion had a concentration of 10% (v/v) and the one coming from coal combustion had a concentration of 14% (v/v). In addition to $CO_2$, flue gases included contaminants such as CO, NOx, and/or SOx coming from coal combustion.

The packed column absorber was operated at 30° C. The absorption solution containing potassium carbonate and TACA was fed at the top of the absorber. As the solution counter currently contacted the flue gas, it absorbed $CO_2$ so the pH of the solution went from 10.2 to 9.1. In order to strip the $CO_2$ out of the absorption solution, the $CO_2$ loaded solution was sent to a stripper where it was heated using a heating medium at a temperature of 85° C. The $CO_2$ was released from the solution as a concentrated $CO_2$ stream. The absorption solution, now a $CO_2$ lean solution, was sent back to the absorber.

TACA enzyme concentrations were varied from 0.2 to 2 g/L. Results are shown in FIG. 16 and indicate that a small enzyme concentration of 2 grams per liter is sufficient to cause an increase in $CO_2$ capture performance by near five-fold under tested conditions. The enzyme was used in the pilot unit for 7 days, 24 h/day, without any activity decrease, even when contacted with gas contaminants such as NOx, CO, and/or SOx, confirming the industrial relevance of TACA for $CO_2$ capture operations.

What is claimed is:

1. A recombinant carbonic anhydrase polypeptide having carbonic anhydrase activity comprising an amino acid sequence having at least 90% identity to SEQ ID NO: 7, and one or more differences as compared to SEQ ID NO: 7 at residue positions selected from 2, 5, 7, 8, 9, 12, 13, 16, 17, 18, 19, 21, 22, 52, 73, 77, 116, 125, 126, 131, 138, 156, 190, 193, and 206.

2. The recombinant polypeptide of claim 1, wherein said amino acid difference is at a position corresponding to position 2, 5, 7, 8, 9, 12, 13, 16, 17, 18, 19, 21, 22, or any combination thereof, of SEQ ID NO: 7.

3. The recombinant carbonic anhydrase polypeptide of claim 1, comprising one or more amino acid differences as compared to SEQ ID NO: 7 selected from: 2Q or 2V; 5C or 5R; 7C, 7F, or 7H; 8C or 8R; 9C, 9P or 9N; 12D, 12R or 12V; G13Q; 16C, 16G, or 16R; 17C; 18V; 19S; 21L, 21D, 21N, 21Q, 21V, or 21G; 22K, 22L, 22P, or 22N; 52I; 73C; 77D; 116N; 125A; 126L; 131I; 138N or 138R; 156E; 190C or 190M; 193S; and 206T.

4. The recombinant carbonic anhydrase polypeptide of claim 1 comprising two or more amino acid differences as compared to SEQ ID NO: 7 which are: 12D and 21Q; 12D and 27T; 12D and 142I; 16C and 167S; 16R and 206T; 16G and 50M; 19S and 138R; 19S and 158G; 150M and 193S; 190M and 193S; 141H and 151C; 8C and 141H; 8C and 151C; 8C, 141H, and 151C; 9P and 21D; 9P and 21N; 9P and 21Q; 9P and 21V; 9P and 21G; 9P and 22P; 8R, 9P, and 22P; 8R, 9P, 22P, and 156E.

5. The recombinant carbonic anhydrase polypeptide of claim 1, further comprising 227Y and 228G.

6. The recombinant carbonic anhydrase polypeptide of claim 1, having at least 90% identity to SEQ ID NO:7.

7. The recombinant carbonic anhydrase polypeptide of claim 1, having at least 95% identity to SEQ ID NO:7.

8. The recombinant carbonic anhydrase polypeptide of claim 1, comprising one or more amino acid differences as compared to SEQ ID NO: 7 selected from:
 (a) 8C or 8R;
 (b) 9C, 9P or 9N;
 (c) 22K, 22L, 22P, or 22N; or
 (d) any combination of (a) to (c),
 wherein said recombinant carbonic anhydrase polypeptide exhibits improved stability in a CO2 capture solvent comprising carbonate ions as compared to the polypeptide of SEQ ID NO:7.

9. A recombinant carbonic anhydrase polypeptide having carbonic anhydrase activity comprising:
 (a) an amino acid sequence having at least 90% identity to SEQ ID NO:7; and
 (b) one or more differences as compared to SEQ ID NO: 7 at residue positions selected from 2, 5, 7, 8, 9, 12, 13, 16, 17, 18, 19, 21, 22, 52, 73, 77, 116, 125, 126, 131, 138, 156, 190, 193, and 206,
 wherein said recombinant carbonic anhydrase polypeptide has improved stability relative to the carbonic anhydrase of SEQ ID NO: 7, following 1 hour of exposure in 1.45 M $K_2CO_3$ pH 10 at 70° C., 85° C. or 90° C.

10. The recombinant polypeptide of claim 9, wherein said amino acid difference is at a position corresponding to position 2, 5, 7, 8, 9, 12, 13, 16, 17, 18, 19, 21, 22, or any combination thereof, of SEQ ID NO: 7.

11. The recombinant carbonic anhydrase polypeptide of claim 9, comprising one or more amino acid differences as compared to SEQ ID NO: 7 selected from: 2Q or 2V; 5C or 5R; 7C, 7F, or 7H; 8C or 8R; 9C, 9P or 9N; 12D, 12R or 12V; G13Q; 16C, 16G, or 16R; 17C; 18V; 19S; 21L, 21D, 21N, 21Q, 21V, or 21G; 22K, 22L, 22P, or 22N; 52I; 73C; 77D; 116N; 125A; 126L; 131I; 138N or 138R; 156E; 190C or 190M; 193S; and 206T.

12. The recombinant carbonic anhydrase polypeptide of claim 9 comprising two or more amino acid differences as compared to SEQ ID NO: 7 which are: 12D and 21Q; 12D and 27T; 12D and 142I; 16C and 167S; 16R and 206T; 16G and 50M; 19S and 138R; 19S and 158G; 150M and 193S; 190M and 193S; 141H and 151C; 8C and 141H; 8C and 151C; 8C, 141H, and 151C; 9P and 21D; 9P and P21N; 9P and 21Q; 9P and 21V; 9P and 21G; 9P and 22P; 8R, 9P, and 22P; 8R, 9P, 22P, and 156E.

13. The recombinant carbonic anhydrase polypeptide of claim 9, further comprising 227Y and 228G.

14. The recombinant carbonic anhydrase polypeptide of claim 9, having at least 85% identity to SEQ ID NO: 7.

15. The recombinant carbonic anhydrase polypeptide of claim 9, having at least 90% identity to SEQ ID NO: 7.

16. The recombinant carbonic anhydrase polypeptide of claim 9, having at least 95% identity to SEQ ID NO: 7.

17. The recombinant carbonic anhydrase polypeptide of claim 9, comprising one or more amino acid differences as compared to SEQ ID NO: 7 selected from:
    (a) 8C or 8R;
    (b) 9C, 9P or 9N;
    (c) 22K, 22L, 22P, or 22N; or
    (d) any combination of (a) to (c).

18. A recombinant variant of a *Thermovibrio ammonificans* carbonic anhydrase polypeptide, said *Thermovibrio ammonificans* carbonic anhydrase polypeptide comprising an amino acid sequence that is at least 90% identical to the sequence of SEQ ID NO: 7, the variant having carbonic anhydrase activity and comprising one or more amino add differences as compared to SEQ ID NO: 7 at residue positions selected from 2, 5, 7, 8, 9, 12, 13, 16, 17, 18, 19, 21, 22, 52, 73, 77, 116, 125, 126, 131, 138, 156, 190, 193, and 206, wherein said variant has improved stability relative to the carbonic anhydrase of SEQ ID NO: 7, following 1 hour of exposure in 1.45 M $K_2CO_3$ pH 10 at 70° C., 85° C. or 90° C.

19. The recombinant carbonic anhydrase polypeptide of claim 18, comprising one or more amino acid differences as compared to SEQ ID NO: 7 selected from: 2Q or 2V; 5C or 5R; 7C, 7F, or 7H; 8C or 8R; 9C, 9P or 9N; 12D, 12R or 12V; G13Q; 16C, 16G, or 16R; 17C; 18V; 19S; 21L, 21D, 21N, 21Q, 21V, or 21G; 27T; 50M; 52I; 73C; 77D; 116N; 125A; 126L; 131I; 138N or 138R; 141H; 142I; 150M; 151C; 156E; 158G; 167S; 173C; 181Y; 190C or 190M; 193S; and 206T.

20. The recombinant carbonic anhydrase polypeptide of claim 18, comprising two or more amino acid differences as compared to SEQ ID NO: 7 which are: 12D and 21Q; 12D and 27T; 12D and 142I; 16C and 167S; 16R and 206T; 16G and 50M; 19S and 138R; 19S and 158G; 150M and 193S; 190M and 193S; 141H and 151C; 8C and 141H; 8C and 151C; 8C, 141H, and 151C; 9P and 21D; 9P and P21N; 9P and 21Q; 9P and 21V; 9P and 21G; 9P and 22P; 8R, 9P, and 22P; 8R, 9P, 22P, and 156E.

* * * * *

SEQUENCE LISTING

```
<160> NUMBER OF SEQ ID NOS: 10

<210> SEQ ID NO 1
<211> LENGTH: 744
<212> TYPE: DNA
<213> ORGANISM: Thermovibrio ammonificans

<400> SEQUENCE: 1
gtgaagagag tattggttac cctcggggct gttgcagcac ttgcaacggg cgcggttgca      60
ggtggaggag cccactgggg ttattccggc agcatcgggc cggagcactg gggagattta     120
agccccgaat accttatgtg taaaatcggt aagaaccaat cgcccataga tattaacagc     180
gccgatgcgg ttaaggcgtg tcttgctccc gttagcgtct actacgtttc agacgcaaag     240
tacgttgtta acaacggcca cacaattaag gttgttatgg ggggaagggg ttacgtggtt     300
gttgacggta agcgctttta cctgaagcag ttccactttc acgccccag cgagcacacc      360 gttaacggca agcactaccc ctttgaagcc cacttcgtcc accttgataa aaacgggaac     420
ataacggtcc ttggcgtttt ctttaaggtt gggaaggaaa accccgagct tgagaaggtg     480
tggcgtgtta tgcccgagga gccgggtcag aagagacacc ttaccgcaag aatcgacccg     540
gagaagctct tgcccgagaa cagggactac tacagatact ccggctctct caccacaccg     600
ccctgctcgg aaggggttag gtggattgtg tttaaagagc cggttgagat gtctcgggag     660
cagcttgaga agttcaggaa agttatgggc tttgacaaca acaggccggt tcagccccctt     720 aatgcaagga aggttatgaa gtag                                            744

<210> SEQ ID NO 2
<211> LENGTH: 247
<212> TYPE: PRT
<213> ORGANISM: Thermovibrio ammonificans
<220> FEATURE:
<221> NAME/KEY: SIGNAL
<222> LOCATION: (1)..(20)

<400> SEQUENCE: 2

Met Lys Arg Val Leu Val Thr Leu Gly Ala Val Ala Ala Leu Ala Thr
1               5                   10                  15

Gly Ala Val Ala Gly Gly Gly Ala His Trp Gly Tyr Ser Gly Ser Ile
                20                  25                  30

Gly Pro Glu His Trp Gly Asp Leu Ser Pro Glu Tyr Leu Met Cys Lys
            35                  40                  45

Ile Gly Lys Asn Gln Ser Pro Ile Asp Ile Asn Ser Ala Asp Ala Val
    50                  55                  60

Lys Ala Cys Leu Ala Pro Val Ser Val Tyr Tyr Val Ser Asp Ala Lys
65                  70                  75                  80

Tyr Val Val Asn Asn Gly His Thr Ile Lys Val Val Met Gly Gly Arg
                85                  90                  95

Gly Tyr Val Val Val Asp Gly Lys Arg Phe Tyr Leu Lys Gln Phe His
                100                 105                 110
```

Phe His Ala Pro Ser Glu His Thr Val Asn Gly Lys His Tyr Pro Phe
            115                 120                 125

Glu Ala His Phe Val His Leu Asp Lys Asn Gly Asn Ile Thr Val Leu
        130                 135                 140

Gly Val Phe Lys Val Gly Lys Glu Asn Pro Glu Leu Glu Lys Val
145                 150                 155                 160

Trp Arg Val Met Pro Glu Pro Gly Gln Lys Arg His Leu Thr Ala
                165                 170                 175

Arg Ile Asp Pro Glu Lys Leu Leu Pro Glu Asn Arg Asp Tyr Tyr Arg
            180                 185                 190

Tyr Ser Gly Ser Leu Thr Thr Pro Pro Cys Ser Glu Gly Val Arg Trp
        195                 200                 205

Ile Val Phe Lys Glu Pro Val Glu Met Ser Arg Glu Gln Leu Glu Lys
    210                 215                 220

Phe Arg Lys Val Met Gly Phe Asp Asn Asn Arg Pro Val Gln Pro Leu
225                 230                 235                 240

Asn Ala Arg Lys Val Met Lys
            245

<210> SEQ ID NO 3
<211> LENGTH: 687
<212> TYPE: DNA
<213> ORGANISM: Artificial Sequence
<220> FEATURE:
<223> OTHER INFORMATION: Nucleic acid sequence encoding SEQ ID NO: 4

<400> SEQUENCE: 3

```
atgggtggcg gtgcacattg gggttatagc ggttcgattg gtccagaaca ttggggtgac      60
ttgtccccgg agtacctgat gtgtaaaatc ggtaagaatc aatccccgat tgatattaat     120
agcgcggacg cggttaaggc atgcctggca ccagttagcg tctactatgt cagcgatgcc     180
aaatacgttg tgaacaacgg ccataccatt aaagttgtga tgggcggtcg tggttatgtc     240
gtcgttgatg gcaaacgttt ctacctgaaa cagttccact ccacgcgcc gagcgagcac      300
acggttaacg gcaagcacta cccgttcgag gctcactttg tgcacctgga taagaatggt     360
aatatcaccg ttctgggcgt gttttttcaag gttggcaagg aaaatccgga gctgaaaaaa    420
gtgtggcgcg ttatgccgga gaaccgggc cagaagcgtc atttgaccgc cgtatcgac       480
cctgagaagc tgctgccgga aaaccgcgac tattaccgtt attctggtag cctgacgact     540
ccgccgtgca gcgagggtgt ccgttggatc gtctttaaag agccggtgga gatgagccgc     600
gaacaactgg agaaatttcg taaagtgatg ggttttgaca caaccgtcc ggtgcagccg      660
ctgaatgcgc gcaaagtcat gaagtaa                                         687
```

<210> SEQ ID NO 4
<211> LENGTH: 228
<212> TYPE: PRT
<213> ORGANISM: Artificial Sequence
<220> FEATURE:
<223> OTHER INFORMATION: Amino acid sequence of wild-type TACA, wherein
      the 20-amino acid N-terminal signal sequence of the wild-type TACA
      is replaced with a methionine residue.

<400> SEQUENCE: 4

Met Gly Gly Gly Ala His Trp Gly Tyr Ser Gly Ser Ile Gly Pro Glu
1               5                   10                  15

His Trp Gly Asp Leu Ser Pro Glu Tyr Leu Met Cys Lys Ile Gly Lys
            20                  25                  30

```
Asn Gln Ser Pro Ile Asp Ile Asn Ser Ala Asp Ala Val Lys Ala Cys
        35                  40                  45

Leu Ala Pro Val Ser Val Tyr Tyr Val Ser Asp Ala Lys Tyr Val Val
 50                  55                  60

Asn Asn Gly His Thr Ile Lys Val Val Met Gly Arg Gly Tyr Val
 65                  70                  75                  80

Val Val Asp Gly Lys Arg Phe Tyr Leu Lys Gln Phe His Phe His Ala
                 85                  90                  95

Pro Ser Glu His Thr Val Asn Gly Lys His Tyr Pro Phe Glu Ala His
                100                 105                 110

Phe Val His Leu Asp Lys Asn Gly Asn Ile Thr Val Leu Gly Val Phe
            115                 120                 125

Phe Lys Val Gly Lys Glu Asn Pro Glu Leu Glu Lys Val Trp Arg Val
130                 135                 140

Met Pro Glu Glu Pro Gly Gln Lys Arg His Leu Thr Ala Arg Ile Asp
145                 150                 155                 160

Pro Glu Lys Leu Leu Pro Glu Asn Arg Asp Tyr Tyr Arg Tyr Ser Gly
                165                 170                 175

Ser Leu Thr Thr Pro Pro Cys Ser Glu Gly Val Arg Trp Ile Val Phe
                180                 185                 190

Lys Glu Pro Val Glu Met Ser Arg Glu Gln Leu Glu Lys Phe Arg Lys
            195                 200                 205

Val Met Gly Phe Asp Asn Asn Arg Pro Val Gln Pro Leu Asn Ala Arg
210                 215                 220

Lys Val Met Lys
225

<210> SEQ ID NO 5
<211> LENGTH: 681
<212> TYPE: DNA
<213> ORGANISM: Artificial Sequence
<220> FEATURE:
<223> OTHER INFORMATION: nucleotide sequence encoding SEQ ID NO: 7

<400> SEQUENCE: 5
atggaacacg aatggggtta tagcggttcg attggtccag aacattgggg tgacttgtcc      60
ccggagtacc tgatgtgtaa atcggtaag aatcaatccc cgattgatat taatagcgcg     120
gacgcggtta aggcatgcct ggcaccagtt agcgtctact atgtcagcga tgccaaatac     180
gttgtgaaca acggccatac cattaaagtt gtgatgggcg gtcgtggtta tgtcgtcgtt     240
gatggcaaac gtttctacct gaaacagttc cacttccacg cgccgagcga gcacacggtt     300
aacggcaagc actacccgtt cgaggctcac tttgtgcacc tggataagaa tggtaatatc     360
accgttctgg gcgtgttttt caaggttggc aaggaaaatc cggagctgga aaaagtgtgg     420
cgcgttatgc cggaagaacc gggccagaag cgtcatttga ccgcccgtat cgaccctgag     480
aagctgctgc cggaaaaccg cgactattac cgttattctg gtagcctgac gactccgccg     540
tgcagcgagg gtgtccgttg gatcgtcttt aaagagccgg tggagatgag ccgcgaacaa     600
ctggagaaat ttcgtaaagt gatgggtttt gacaacaacc gtccggtgca gccgctgaat     660
gcgcgcaaag tcatgaagta a                                               681

<210> SEQ ID NO 6
<211> LENGTH: 226
<212> TYPE: PRT
<213> ORGANISM: Artificial Sequence
```

```
<220> FEATURE:
<223> OTHER INFORMATION: Amino acid sequence of an N-terminal truncated
      wild-type TACA variant displaying higher expression in a bacterial
      host, wherein the first six amino acids of SEQ ID NO: 4 ("MGGGAH")
      are replaced with the four residues "MEHE".

<400> SEQUENCE: 6

Met Glu His Glu Trp Gly Tyr Ser Gly Ser Ile Gly Pro Glu His Trp
1               5                   10                  15

Gly Asp Leu Ser Pro Glu Tyr Leu Met Cys Lys Ile Gly Lys Asn Gln
                20                  25                  30

Ser Pro Ile Asp Ile Asn Ser Ala Asp Ala Val Lys Ala Cys Leu Ala
            35                  40                  45

Pro Val Ser Val Tyr Tyr Val Ser Asp Ala Lys Tyr Val Val Asn Asn
        50                  55                  60

Gly His Thr Ile Lys Val Val Met Gly Arg Gly Tyr Val Val
65                  70                  75                  80

Asp Gly Lys Arg Phe Tyr Leu Lys Gln Phe His Phe His Ala Pro Ser
                85                  90                  95

Glu His Thr Val Asn Gly Lys His Tyr Pro Phe Glu Ala His Phe Val
                100                 105                 110

His Leu Asp Lys Asn Gly Asn Ile Thr Val Leu Gly Val Phe Phe Lys
            115                 120                 125

Val Gly Lys Glu Asn Pro Glu Leu Glu Lys Val Trp Arg Val Met Pro
130                 135                 140

Glu Glu Pro Gly Gln Lys Arg His Leu Thr Ala Arg Ile Asp Pro Glu
145                 150                 155                 160

Lys Leu Leu Pro Glu Asn Arg Asp Tyr Tyr Arg Tyr Ser Gly Ser Leu
                165                 170                 175

Thr Thr Pro Pro Cys Ser Glu Gly Val Arg Trp Ile Val Phe Lys Glu
                180                 185                 190

Pro Val Glu Met Ser Arg Glu Gln Leu Glu Lys Phe Arg Lys Val Met
            195                 200                 205

Gly Phe Asp Asn Asn Arg Pro Val Gln Pro Leu Asn Ala Arg Lys Val
210                 215                 220

Met Lys
225

<210> SEQ ID NO 7
<211> LENGTH: 226
<212> TYPE: PRT
<213> ORGANISM: Artificial Sequence
<220> FEATURE:
<223> OTHER INFORMATION: Amino acid sequence of an N-terminal truncated
      wild-type TACA variant displaying higher expression in a bacterial
      host, wherein the first six amino acids of SEQ ID NO: 4 ("MGGGAH")
      are replaced with the four residues "MEHE"

<400> SEQUENCE: 7

Met Glu His Glu Trp Gly Tyr Ser Gly Ser Ile Gly Pro Glu His Trp
1               5                   10                  15

Gly Asp Leu Ser Pro Glu Tyr Leu Met Cys Lys Ile Gly Lys Asn Gln
                20                  25                  30

Ser Pro Ile Asp Ile Asn Ser Ala Asp Ala Val Lys Ala Cys Leu Ala
            35                  40                  45

Pro Val Ser Val Tyr Tyr Val Ser Asp Ala Lys Tyr Val Val Asn Asn
        50                  55                  60
```

```
Gly His Thr Ile Lys Val Val Met Gly Gly Arg Gly Tyr Val Val Val
65                  70                  75                  80

Asp Gly Lys Arg Phe Tyr Leu Lys Gln Phe His Phe His Ala Pro Ser
                85                  90                  95

Glu His Thr Val Asn Gly Lys His Tyr Pro Phe Glu Ala His Phe Val
                100                 105                 110

His Leu Asp Lys Asn Gly Asn Ile Thr Val Leu Gly Val Phe Phe Lys
                115                 120                 125

Val Gly Lys Glu Asn Pro Glu Leu Glu Lys Val Trp Arg Val Met Pro
        130                 135                 140

Glu Glu Pro Gly Gln Lys Arg His Leu Thr Ala Arg Ile Asp Pro Glu
145                 150                 155                 160

Lys Leu Leu Pro Glu Asn Arg Asp Tyr Tyr Arg Tyr Ser Gly Ser Leu
                165                 170                 175

Thr Thr Pro Pro Cys Ser Glu Gly Val Arg Trp Ile Val Phe Lys Glu
                180                 185                 190

Pro Val Glu Met Ser Arg Glu Gln Leu Glu Lys Phe Arg Lys Val Met
        195                 200                 205

Gly Phe Asp Asn Asn Arg Pro Val Gln Pro Leu Asn Ala Arg Lys Val
        210                 215                 220

Met Lys
225

<210> SEQ ID NO 8
<211> LENGTH: 227
<212> TYPE: PRT
<213> ORGANISM: Sulfurihydrogenibium sp.

<400> SEQUENCE: 8

Met Glu His Glu Trp Ser Tyr Glu Gly Glu Lys Gly Pro Glu His Trp
1               5                   10                  15

Ala Gln Leu Lys Pro Glu Phe Phe Trp Cys Lys Leu Lys Asn Gln Ser
                20                  25                  30

Pro Ile Asn Ile Asp Lys Lys Tyr Lys Val Lys Ala Asn Leu Pro Lys
                35                  40                  45

Leu Asn Leu Tyr Tyr Lys Thr Ala Lys Glu Ser Glu Val Val Asn Asn
50                  55                  60

Gly His Thr Ile Gln Ile Asn Ile Lys Glu Asp Asn Thr Leu Asn Tyr
65                  70                  75                  80

Leu Gly Glu Lys Tyr Gln Leu Lys Gln Phe His Phe His Thr Pro Ser
                85                  90                  95

Glu His Thr Ile Glu Lys Lys Ser Tyr Pro Leu Glu Ile His Phe Val
                100                 105                 110

His Lys Thr Glu Asp Gly Lys Ile Leu Val Val Gly Val Met Ala Lys
                115                 120                 125

Leu Gly Lys Thr Asn Lys Glu Leu Asp Lys Ile Leu Asn Val Ala Pro
        130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
                180                 185                 190

Ile Ser Ile Ser Lys Gln Gln Leu Glu Lys Leu Lys Ser Val Met Val
        195                 200                 205
```

Asn Pro Asn Asn Arg Pro Val Gln Glu Ile Asn Ser Arg Trp Ile Ile
            210                 215                 220

Glu Gly Phe
225

<210> SEQ ID NO 9
<211> LENGTH: 227
<212> TYPE: PRT
<213> ORGANISM: Artificial Sequence
<220> FEATURE:
<223> OTHER INFORMATION: SspCA 6M1

<400> SEQUENCE: 9

Met Glu His Glu Trp Ser Tyr Glu Gly Glu Lys Gly Pro Glu His Trp
1               5                   10                  15

Ala Phe Leu Arg Pro Glu Phe Phe Trp Cys Lys Leu Lys Asn Gln Ser
            20                  25                  30

Pro Ile Asn Ile Asp Ser Lys Tyr Lys Val Lys Ala Asn Leu Pro Lys
        35                  40                  45

Leu Asn Leu Tyr Tyr Lys Thr Ala Leu Glu Ser Glu Val Val Asn Asn
    50                  55                  60

Gly His Thr Ile Gln Ile Asn Ile Lys Glu Asp Asn Thr Leu Asn Tyr
65                  70                  75                  80

Leu Cys Glu Lys Tyr Gln Leu Lys Gln Phe His Phe His Thr Pro Ser
                85                  90                  95

Glu His Thr Val Glu Lys Lys Ser Tyr Pro Leu Glu Ile His Phe Val
            100                 105                 110

His Lys Thr Glu Asp Gly Lys Ile Leu Val Val Gly Val Met Ala Lys
        115                 120                 125

Leu Gly Lys Thr Asn Lys Glu Leu Asp Lys Ile Leu Asn Val Ala Pro
    130                 135                 140

Ala Glu Glu Gly Glu Lys Ile Leu Asp Lys Asn Leu Asn Leu Asn Asn
145                 150                 155                 160

Leu Ile Pro Lys Asp Lys Arg Tyr Met Thr Tyr Ser Gly Ser Leu Thr
                165                 170                 175

Thr Pro Pro Cys Thr Glu Gly Val Arg Trp Ile Val Leu Lys Lys Pro
            180                 185                 190

Ile Ser Ile Ser Lys Gln Gln Leu Glu Lys Leu Lys Ser Val Met Val
        195                 200                 205

Asn Pro Asn Asn Arg Pro Val Gln Glu Ile Asn Ser Arg Trp Ile Ile
    210                 215                 220

Glu Gly Phe
225

<210> SEQ ID NO 10
<211> LENGTH: 222
<212> TYPE: PRT
<213> ORGANISM: Artificial Sequence
<220> FEATURE:
<223> OTHER INFORMATION: Amino acid sequence of wild-type TACA beginning
      at the highly conserved tryptophan residue at position 26 of SEQ
      ID NO: 2, position 7 of SEQ ID NO: 4, or position 5 of SEQ ID NO:
      7

<400> SEQUENCE: 10

Trp Gly Tyr Ser Gly Ser Ile Gly Pro Glu His Trp Gly Asp Leu Ser
1               5                   10                  15

Pro Glu Tyr Leu Met Cys Lys Ile Gly Lys Asn Gln Ser Pro Ile Asp
            20                  25                  30

```
Ile Asn Ser Ala Asp Ala Val Lys Ala Cys Leu Ala Pro Val Ser Val
    35                  40                  45
Tyr Tyr Val Ser Asp Ala Lys Tyr Val Val Asn Asn Gly His Thr Ile
    50                  55                  60
Lys Val Val Met Gly Gly Arg Gly Tyr Val Val Asp Gly Lys Arg
65                  70                  75                  80
Phe Tyr Leu Lys Gln Phe His Phe His Ala Pro Ser Glu His Thr Val
                85                  90                  95
Asn Gly Lys His Tyr Pro Phe Glu Ala His Phe Val His Leu Asp Lys
            100                 105                 110
Asn Gly Asn Ile Thr Val Leu Gly Val Phe Phe Lys Val Gly Lys Glu
            115                 120                 125
Asn Pro Glu Leu Glu Lys Val Trp Arg Val Met Pro Glu Glu Pro Gly
    130                 135                 140
Gln Lys Arg His Leu Thr Ala Arg Ile Asp Pro Glu Lys Leu Leu Pro
145                 150                 155                 160
Glu Asn Arg Asp Tyr Tyr Arg Tyr Ser Gly Ser Leu Thr Thr Pro Pro
                165                 170                 175
Cys Ser Glu Gly Val Arg Trp Ile Val Phe Lys Glu Pro Val Glu Met
            180                 185                 190
Ser Arg Glu Gln Leu Glu Lys Phe Arg Lys Val Met Gly Phe Asp Asn
    195                 200                 205
Asn Arg Pro Val Gln Pro Leu Asn Ala Arg Lys Val Met Lys
    210                 215                 220
```